(12) United States Patent
Falo, Jr. et al.

(10) Patent No.: US 12,214,150 B2
(45) Date of Patent: Feb. 4, 2025

(54) MICRONEEDLE ARRAYS WITH UNDERCUT FEATURES FOR CUTANEOUS AND NON-CUTANEOUS DRUG DELIVERY

(71) Applicant: University of Pittsburgh—Of the Commonwealth System of Higher Education, Pittsburgh, PA (US)

(72) Inventors: Louis D. Falo, Jr., Wexford, PA (US); Emrullah Korkmaz, Pittsburgh, PA (US)

(73) Assignee: University of Pittsburgh—Of the Commonwealth System of Higher Education, Pittsburgh, PA (US)

(*) Notice: Subject to any disclaimer, the term of this patent is extended or adjusted under 35 U.S.C. 154(b) by 247 days.

(21) Appl. No.: 17/611,486

(22) PCT Filed: May 15, 2020

(86) PCT No.: PCT/US2020/033235
§ 371 (c)(1),
(2) Date: Nov. 15, 2021

(87) PCT Pub. No.: WO2020/232394
PCT Pub. Date: Nov. 19, 2020

(65) Prior Publication Data
US 2022/0241570 A1 Aug. 4, 2022

Related U.S. Application Data

(60) Provisional application No. 62/848,939, filed on May 16, 2019.

(51) Int. Cl.
*B29C 33/44* (2006.01)
*A61M 37/00* (2006.01)
(Continued)

(52) U.S. Cl.
CPC ..... *A61M 37/0015* (2013.01); *B29C 33/3835* (2013.01); *B29C 33/3842* (2013.01);
(Continued)

(58) Field of Classification Search
CPC ...... A61M 37/0015; A61M 2037/0023; A61M 2037/0046; A61M 2037/0053;
(Continued)

(56) References Cited

U.S. PATENT DOCUMENTS 5,312,456 A 5/1994 Reed
5,658,515 A 8/1997 Lee et al.
(Continued)

FOREIGN PATENT DOCUMENTS

| CN | 147590 A | 3/2004 |
| CN | 1621102 | 6/2005 |

(Continued)

OTHER PUBLICATIONS

Park et al., "Polymer microneedles for controlled-release drug delivery," *Pharmaceutical Research* 23(5): 1008-1019, May 2006.
(Continued)

*Primary Examiner* — Leo B Tentoni
(74) *Attorney, Agent, or Firm* — Klarquist Sparkman, LLP

(57) ABSTRACT

The disclosed methods relate to forming microneedle arrays from a production mold that comprises a flexible mold material. The disclosed methods can be used to reproducibly manufacture undercut dissolvable and coated microneedle arrays with various shapes and structures.

20 Claims, 14 Drawing Sheets

(51) Int. Cl.
*B29C 33/38* (2006.01)
*B29C 33/40* (2006.01)
*B29C 33/50* (2006.01)
*B29K 105/00* (2006.01)
*B29L 31/00* (2006.01)

(52) U.S. Cl.
CPC ...... *B29C 33/3857* (2013.01); *B29C 33/3878* (2013.01); *B29C 33/405* (2013.01); *B29C 33/50* (2013.01); *A61M 2037/0023* (2013.01); *A61M 2037/0053* (2013.01); *B29K 2105/0035* (2013.01); *B29K 2995/006* (2013.01); *B29K 2995/0062* (2013.01); *B29L 2031/7544* (2013.01); *B29L 2031/756* (2013.01)

(58) Field of Classification Search
CPC ............ B29C 33/3835; B29C 33/3842; B29C 33/3857; B29C 33/3878; B29C 33/405; B29C 33/44; B29K 2105/003; B29K 2995/006; B29K 2995/0062; B29L 2031/7544
USPC ......... 264/219, 227, 318, 334, 337; 604/173
See application file for complete search history.

(56) References Cited

U.S. PATENT DOCUMENTS

| | | |
|---|---|---|
| 6,331,266 B1 | 12/2001 | Powell et al. |
| 6,451,240 B1 | 9/2002 | Sherman et al. |
| 6,511,463 B1 | 1/2003 | Wood et al. |
| 6,565,871 B2 | 5/2003 | Roser et al. |
| 6,611,707 B1 | 8/2003 | Prausnitz et al. |
| 6,623,707 B1 | 9/2003 | Addiego et al. |
| 6,652,478 B1 | 11/2003 | Gartstein et al. |
| 6,656,147 B1 | 12/2003 | Gertsek et al. |
| 6,663,820 B2 | 12/2003 | Arias et al. |
| 6,743,211 B1 | 6/2004 | Prausnitz et al. |
| 6,767,211 B2 | 7/2004 | Hall et al. |
| 6,881,203 B2 | 4/2005 | Delmore et al. |
| 6,899,838 B2 | 5/2005 | Lastovich |
| 6,908,453 B2 | 6/2005 | Fleming et al. |
| 6,924,087 B2 | 8/2005 | Yeshurun et al. |
| 6,931,277 B1 | 8/2005 | Yuzhakov et al. |
| 7,052,268 B2 | 5/2006 | Powell et al. |
| 7,132,054 B1 | 11/2006 | Kravitz et al. |
| 7,211,062 B2 | 5/2007 | Kwon |
| 7,226,439 B2 | 6/2007 | Prausnitz et al. |
| 7,285,113 B2 | 10/2007 | Yeshurun |
| 7,315,758 B2 | 1/2008 | Kwiatkowski et al. |
| 7,316,665 B2 | 1/2008 | Laurent et al. |
| 7,332,197 B2 | 2/2008 | Wood et al. |
| 7,364,568 B2 | 4/2008 | Angel et al. |
| 7,416,541 B2 | 8/2008 | Yuzhakov et al. |
| 7,429,333 B2 | 9/2008 | Chiou et al. |
| 7,473,247 B2 | 1/2009 | Mikszta et al. |
| 7,497,980 B2 | 3/2009 | Xu et al. |
| 7,560,036 B2 | 7/2009 | Golubovic-Liakopoulos et al. |
| 7,578,954 B2 | 8/2009 | Gartstein et al. |
| 7,588,552 B2 | 9/2009 | Yeshurun et al. |
| 7,591,806 B2 | 9/2009 | Xu |
| 7,611,481 B2 | 11/2009 | Cleary et al. |
| 7,648,484 B2 | 1/2010 | Yeshurun et al. |
| 7,651,475 B2 | 1/2010 | Angel et al. |
| 7,658,728 B2 | 2/2010 | Yuzhakov |
| 7,699,819 B2 | 4/2010 | Yeung et al. |
| 7,731,968 B2 | 6/2010 | Mikszta et al. |
| D619,245 S | 7/2010 | Moga et al. |
| 7,753,888 B2 | 7/2010 | Mukerjee et al. |
| 7,763,203 B2 | 7/2010 | Arias et al. |
| 7,785,301 B2 | 8/2010 | Yuzhakov |
| 7,846,488 B2 | 12/2010 | Johnson et al. |
| 7,850,657 B2 | 12/2010 | Yeshurun et al. |
| D638,534 S | 5/2011 | Moga et al. |
| 7,942,827 B2 | 5/2011 | Mir et al. |
| 8,052,633 B2 | 11/2011 | Kendall |
| 8,057,842 B2 | 11/2011 | Choi et al. |
| 8,062,573 B2 | 11/2011 | Kwon |
| 8,062,835 B2 | 11/2011 | Tomono |
| 8,088,321 B2 | 1/2012 | Ferguson et al. |
| 8,101,114 B2 | 1/2012 | Park et al. |
| 8,137,736 B2 | 3/2012 | Zhu et al. |
| 8,162,901 B2 | 4/2012 | Gonnelli et al. |
| 8,167,852 B2 | 5/2012 | Quan et al. |
| 8,172,815 B2 | 5/2012 | Down et al. |
| 8,192,787 B2 | 6/2012 | Kirby |
| 8,216,190 B2 | 7/2012 | Gartstein et al. |
| 8,236,368 B2 | 8/2012 | Jung et al. |
| 8,246,582 B2 | 8/2012 | Angel et al. |
| 8,246,893 B2 | 8/2012 | Ferguson et al. |
| 8,250,729 B2 | 8/2012 | Lee et al. |
| 8,257,324 B2 | 9/2012 | Prausnitz et al. |
| 8,267,889 B2 | 9/2012 | Cantor et al. |
| 8,328,757 B2 | 12/2012 | Beebe et al. |
| 8,353,861 B2 | 1/2013 | Tobinaga et al. |
| 8,354,033 B2 | 1/2013 | Scholten et al. |
| 8,361,037 B2 | 1/2013 | Gonnelli |
| 8,366,677 B2 | 2/2013 | Kaspar et al. |
| 8,376,984 B2 | 2/2013 | James |
| 8,402,629 B2 | 3/2013 | Lee et al. |
| 8,414,548 B2 | 4/2013 | Yuzhakov |
| 8,414,959 B2 | 4/2013 | Hye-Ok et al. |
| 8,419,708 B2 | 4/2013 | Tokumoto et al. |
| 8,444,622 B2 | 5/2013 | Eckhoff et al. |
| 8,449,807 B2 | 5/2013 | Ferguson et al. |
| 8,454,844 B2 | 6/2013 | Yeshurun et al. |
| 8,491,534 B2 | 7/2013 | Takada |
| 8,506,530 B2 | 8/2013 | Laermer et al. |
| 8,506,980 B2 | 8/2013 | Takada |
| 8,540,672 B2 | 9/2013 | McAllister |
| 8,545,741 B2 | 10/2013 | Jung et al. |
| 8,551,391 B2 | 10/2013 | Chang et al. |
| 8,554,317 B2 | 10/2013 | Duan |
| 8,560,059 B2 | 10/2013 | Hoarau et al. |
| 8,579,862 B2 | 11/2013 | Kobayashi et al. |
| 8,603,384 B2 | 12/2013 | Luttge et al. |
| 8,636,696 B2 | 1/2014 | Ross et al. |
| 8,637,136 B2 | 1/2014 | Ferguson et al. |
| 8,671,544 B2 | 3/2014 | Xu et al. |
| 8,696,637 B2 | 4/2014 | Ross |
| 8,696,638 B2 | 4/2014 | Terahara et al. |
| 8,708,966 B2 | 4/2014 | Allen et al. |
| 8,734,697 B2 | 5/2014 | Chen et al. |
| 8,741,377 B2 | 6/2014 | Choi et al. |
| 8,747,362 B2 | 6/2014 | Terahara et al. |
| 8,758,298 B2 | 6/2014 | Cantor et al. |
| 8,771,781 B2 | 7/2014 | Tokumoto et al. |
| 8,784,368 B2 | 7/2014 | Eckhoff et al. |
| 8,784,373 B2 | 7/2014 | Gharib et al. |
| 8,784,383 B2 | 7/2014 | Cole et al. |
| 8,784,384 B2 | 7/2014 | Boyden et al. |
| 8,784,385 B2 | 7/2014 | Boyden et al. |
| 8,784,860 B2 | 7/2014 | Falotico et al. |
| 8,785,400 B2 | 7/2014 | Levetan et al. |
| 8,788,037 B2 | 7/2014 | Della Rocca et al. |
| 8,788,211 B2 | 7/2014 | Boyden et al. |
| 8,788,212 B2 | 7/2014 | Boyden et al. |
| 8,790,257 B2 | 7/2014 | Libbus et al. |
| 8,790,259 B2 | 7/2014 | Katra et al. |
| 8,790,658 B2 | 7/2014 | Cigarini et al. |
| 8,791,062 B2 | 7/2014 | Hsu et al. |
| 8,791,107 B2 | 7/2014 | Chang et al. |
| 8,793,075 B2 | 8/2014 | Boyden et al. |
| 8,795,174 B2 | 8/2014 | Manicka et al. |
| 8,795,201 B2 | 8/2014 | Escutia et al. |
| 8,795,230 B2 | 8/2014 | Schoonmaker et al. |
| 8,795,234 B2 | 8/2014 | Kadamus et al. |
| 8,795,259 B2 | 8/2014 | Beebe et al. |
| 8,796,436 B2 | 8/2014 | Manoharan et al. |
| 8,798,722 B2 | 8/2014 | Rylander et al. |
| 8,798,932 B2 | 8/2014 | Boyden et al. |
| 8,798,933 B2 | 8/2014 | Boyden et al. |
| 8,821,446 B2 | 9/2014 | Trautman et al. |
| 8,821,779 B2 | 9/2014 | Ferguson et al. |

(56) References Cited

U.S. PATENT DOCUMENTS

| | | | |
|---|---|---|---|
| 8,834,423 | B2 | 9/2014 | Falo, Jr. |
| 10,441,768 | B2 | 10/2019 | Falo, Jr. |
| 2002/0082543 | A1 | 6/2002 | Park et al. |
| 2002/0193729 | A1 | 12/2002 | Cormier et al. |
| 2002/0198509 | A1 | 12/2002 | Mikszta et al. |
| 2004/0058882 | A1 | 3/2004 | Eriksson et al. |
| 2005/0008683 | A1 | 1/2005 | Mikszta et al. |
| 2005/0013221 | A1 | 1/2005 | Takanobu |
| 2005/0019918 | A1 | 1/2005 | Sumimoto et al. |
| 2005/0065463 | A1 | 3/2005 | Tobinaga et al. |
| 2005/0089553 | A1 | 4/2005 | Cormier et al. |
| 2005/0095298 | A1 | 5/2005 | Gronlund et al. |
| 2007/0161964 | A1 | 7/2007 | Yuzhakov |
| 2007/0260201 | A1 | 11/2007 | Prausnitz et al. |
| 2007/0299388 | A1 | 12/2007 | Chan et al. |
| 2008/0009763 | A1 | 1/2008 | Chiou et al. |
| 2008/0208134 | A1 | 8/2008 | Tomono |
| 2008/0213461 | A1 | 9/2008 | Gill et al. |
| 2008/0214987 | A1 | 9/2008 | Xu |
| 2008/0221532 | A1 | 9/2008 | Ogawa |
| 2008/0269658 | A1 | 10/2008 | Vinton et al. |
| 2008/0269685 | A1 | 10/2008 | Singh et al. |
| 2009/0017210 | A1 | 1/2009 | Andrianov et al. |
| 2009/0054842 | A1 | 2/2009 | Yeshurun et al. |
| 2009/0232855 | A1 | 9/2009 | Sang et al. |
| 2010/0042137 | A1 | 2/2010 | Oronsky et al. |
| 2010/0228203 | A1 | 9/2010 | Quan et al. |
| 2010/0233093 | A1 | 9/2010 | Oh et al. |
| 2011/0046575 | A1 | 2/2011 | Takada |
| 2011/0098651 | A1* | 4/2011 | Falo, Jr. ............ A61M 37/0015 604/173 |
| 2011/0172605 | A1 | 7/2011 | Berenschot et al. |
| 2011/0230736 | A1 | 9/2011 | Tepper et al. |
| 2012/0064124 | A1 | 3/2012 | McClain et al. |
| 2012/0078189 | A1 | 3/2012 | Ogawa et al. |
| 2012/0123341 | A1 | 5/2012 | Birchall et al. |
| 2012/0265145 | A1 | 10/2012 | Mefti et al. |
| 2013/0072902 | A1 | 3/2013 | Takada et al. |
| 2013/0096532 | A1 | 4/2013 | Ozel et al. |
| 2013/0165772 | A1 | 6/2013 | Traverso et al. |
| 2013/0190794 | A1 | 7/2013 | Kendall et al. |
| 2013/0338632 | A1 | 12/2013 | Kaplan et al. |
| 2014/0066843 | A1 | 3/2014 | Zhang et al. |
| 2014/0142492 | A1 | 5/2014 | Jung et al. |
| 2014/0142541 | A1 | 5/2014 | Yan et al. |
| 2014/0200511 | A1 | 7/2014 | Boyden et al. |
| 2014/0336487 | A1* | 11/2014 | Wang ............... A61B 5/6833 600/352 |
| 2015/0030642 | A1 | 1/2015 | Wu et al. |
| 2015/0126923 | A1 | 5/2015 | Falo, Jr. |
| 2016/0158512 | A1 | 6/2016 | Tamaru et al. |
| 2016/0271380 | A1* | 9/2016 | Poon ............... A61M 37/0015 |
| 2017/0274196 | A1 | 9/2017 | Nordon et al. |
| 2018/0236215 | A1* | 8/2018 | Liu ................. A61M 37/0015 |
| 2018/0272621 | A1 | 9/2018 | Falo, Jr. et al. |
| 2018/0304062 | A1 | 10/2018 | Falo, Jr. et al. |
| 2018/0333898 | A1 | 11/2018 | Francis et al. |
| 2019/0000966 | A1 | 1/2019 | Falo, Jr. et al. |
| 2019/0015650 | A1 | 1/2019 | Jaklenec et al. |
| 2019/0255307 | A1 | 8/2019 | Falo, Jr. et al. |
| 2020/0345994 | A1* | 11/2020 | Lalwani ............ A61M 37/0015 |

FOREIGN PATENT DOCUMENTS

| | | |
|---|---|---|
| CN | 104117137 A | 10/2014 |
| JP | 2005-35945 | 2/2005 |
| JP | 2010-069253 A | 4/2010 |
| JP | 2011-224332 | 11/2011 |
| JP | 2016-030072 A | 3/2016 |
| JP | 2017-213171 A | 12/2017 |
| KR | 101832716 B1 | 2/2018 |
| RU | 2679107 C2 | 2/2019 |
| WO | WO 98/00194 | 1/1998 |
| WO | WO 98/29134 | 7/1998 |
| WO | WO 2005/025413 | 9/2005 |
| WO | WO 2007/080596 A2 | 7/2007 |
| WO | WO 2007/113648 A2 | 10/2007 |
| WO | WO 2008/091602 | 7/2008 |
| WO | WO 2008/114218 A2 | 9/2008 |
| WO | WO 2009-004995 | 1/2009 |
| WO | WO 2009/009004 | 1/2009 |
| WO | WO 2009/040548 | 4/2009 |
| WO | WO 2009/081122 | 7/2009 |
| WO | WO 2009/094394 | 7/2009 |
| WO | WO 2010/022252 | 2/2010 |
| WO | WO 2010/071918 | 7/2010 |
| WO | WO 2010/141377 | 12/2010 |
| WO | WO 2011/135531 | 11/2011 |
| WO | WO 2011/135532 A2 | 11/2011 |
| WO | WO 2011/135533 A2 | 11/2011 |
| WO | WO 2012/020332 A2 | 2/2012 |
| WO | WO 2012/054582 | 4/2012 |
| WO | WO 2012/153266 | 11/2012 |
| WO | WO 2013/033400 | 3/2013 |
| WO | WO 2013/166162 | 11/2013 |
| WO | WO 2014/012147 | 1/2014 |
| WO | WO 2015/016235 A1 | 2/2015 |
| WO | WO 2015/048777 | 4/2015 |

OTHER PUBLICATIONS

Bandyopadhyay et al. "Skin codelivery of contact sensitizers and neurokinin-1 receptor antagonists integrated in microneedle arrays suppresses allergic contact dermatitis," *Journal of Allergy and Clinical Immunology* pp. 114-130, Jan. 2022.

Cobleigh et al., "A phase II study of Adriamycin in previously untreated squamous cell carcinoma of the head and neck," *Cancer* 56(11): 2573-2575, 1985.

Filiz et al., "Micromilling of microbarbs for medical implants," *International Journal of Machine Tools and Manufacture* 48(3-4): 459-472, 2008.

International Search Report and Written Opinion, mailed Aug. 7, 2020, issued for International Patent Application No. PCT/US2020/033235, 17 pages.

Kim et al., "Microneedles for drug and vaccine delivery," *Advanced Drug Delivery Reviews* 64(14): 1547-1568, 2012.

Khodadust et al., "Development of poly (I: C) modified doxorubicin loaded magnetic dendrimer nanoparticles for targeted combination therapy," *Biomedicine & Pharmacotherapy* 68(8): 979-987, 2014.

Lee et al., "Dissolving microneedles for transdermal drug delivery," *Biomaterials* 29(13): 2113-2124, 2008.

Lee et al., "Transdermal drug delivery system using microneedles," Korean Journal of Skin Barrier Research 15(1): 22-33, Jun. 2013 (with English-language machine translation).

Ma et al., "Poly (I: C) inhibits melanoma metastasis and enhances chemerin expression and NK cell recruitment via a RIG-like helicase innate immune/MAVS-dependent mechanism," In C38. Pulmonary and Systemic Inflammation, American Thoracic Society, pp. A4165-A4165, 2013.

Shiozuka et al., "Transdermal delivery of adriamycin to transplanted Ehrlich ascites tumor in mice," *Pharmaceutics* 5(3): 385-391, 2013.

Von Boehmer et al., "Therapeutic opportunities for manipulating T Reg cells in autoimmunity and cancer," *Nature Reviews Drug discovery* 12(1): 51-63, Jan. 2013.

Xie et al., "Toll-like receptor 2 mediates invasion via activating NF-κB in MDA-MB-231 breast cancer cells," *Biochemical and Biophysical Research Communications* 379(4): 1027-1032, 2009.

Salem et al., "Defining the antigen-specific T-cell response to vaccination and poly (I: C)/TLR3 signaling: evidence of enhanced primary and memory CD8 T-cell responses and antitumor immunity," *Journal of Immunotherapy* 28(3): 220-228, 2005.

\* cited by examiner

FIG. 9A  FIG. 9B  FIG. 9C
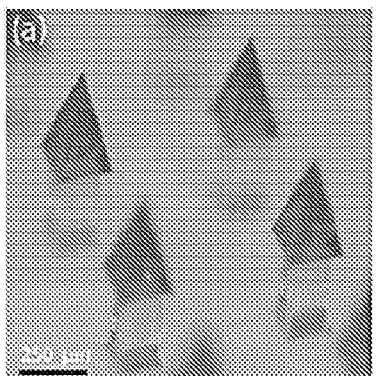 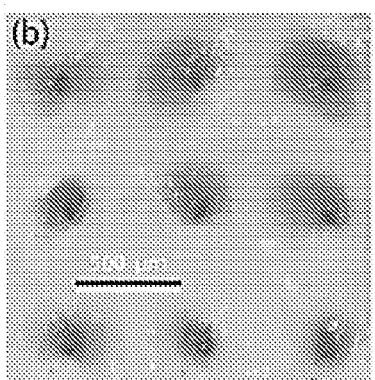 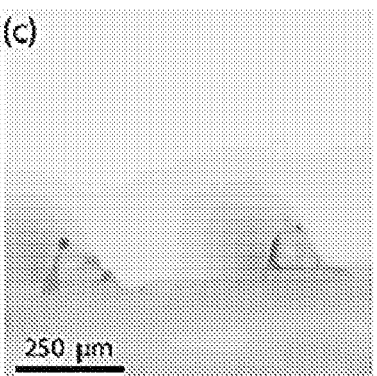
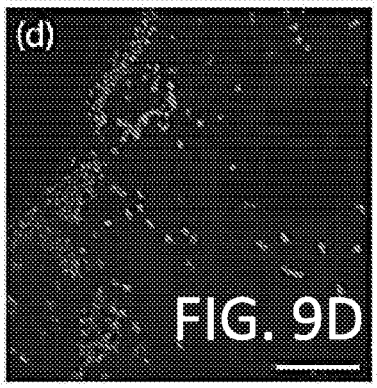 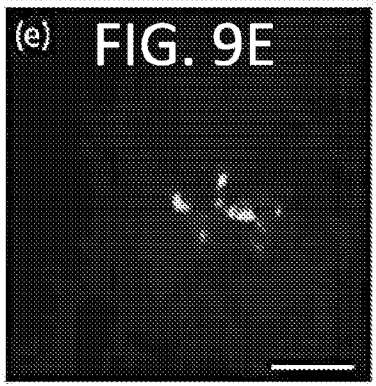 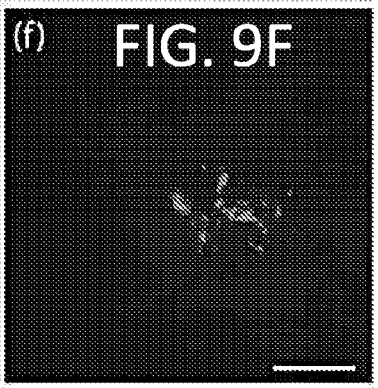
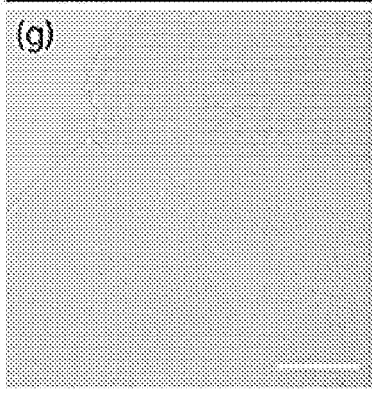 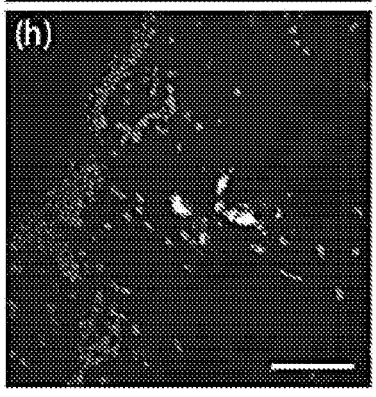 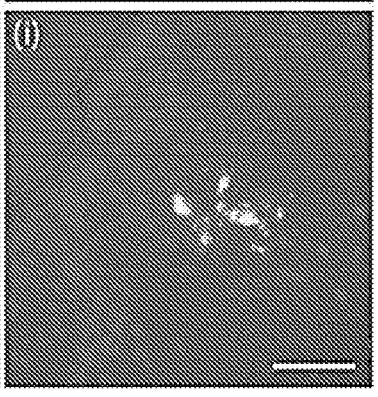
FIG. 9G  FIG. 9H  FIG. 9I

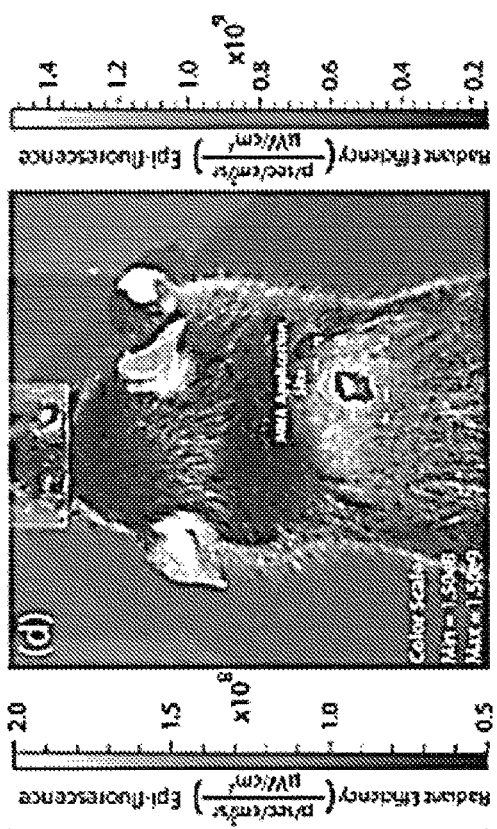
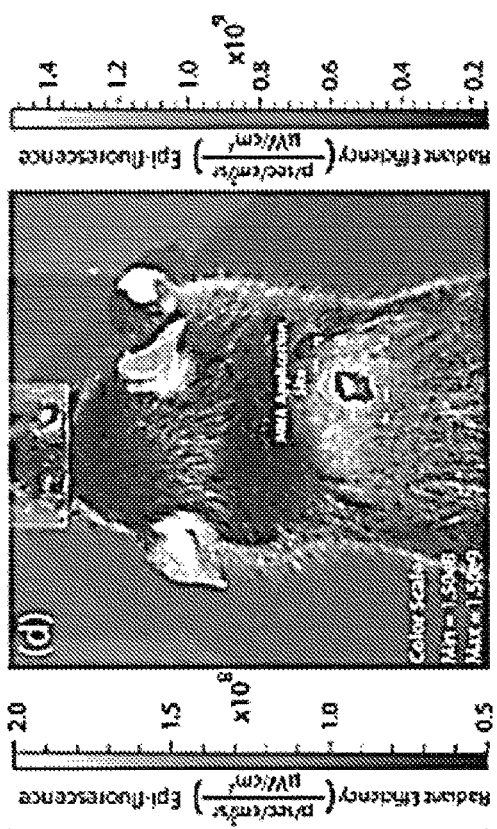
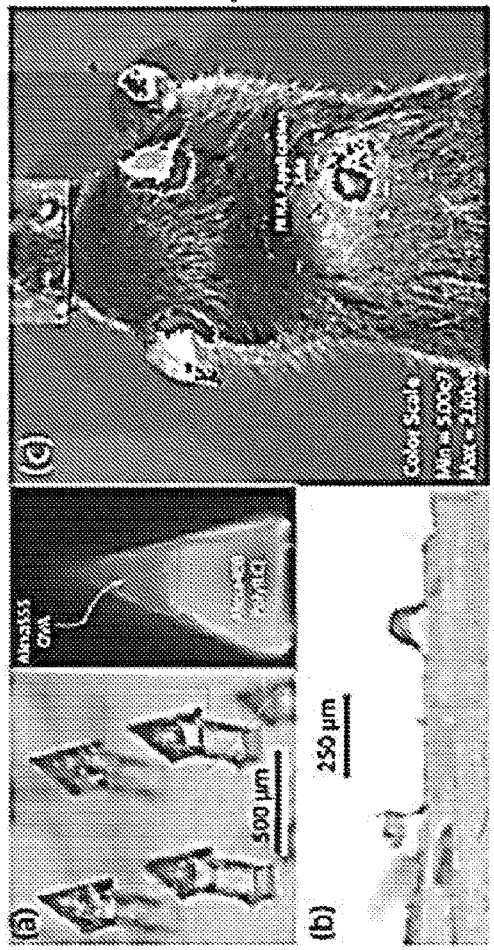
FIG. 10A  FIG. 10B  FIG. 10C  FIG. 10D

MICRONEEDLE ARRAYS WITH UNDERCUT FEATURES FOR CUTANEOUS AND NON-CUTANEOUS DRUG DELIVERY

CROSS REFERENCE TO RELATED APPLICATIONS

This is the U.S. National Stage of International Application No. PCT/US2020/033235, filed May 15, 2020, which was published in English under PCT Article 21(2), which in turn claims the benefit of U.S. Provisional Application No. 62/848,939, filed May 16, 2019. The provisional application is incorporated herein in its entirety.

ACKNOWLEDGMENT OF GOVERNMENT SUPPORT

This invention was made with government support under grant numbers AR071277 and AR074285 awarded by the National Institutes of Health. The government has certain rights in the invention.

FIELD

This disclosure is directed to microneedle arrays and, in particular, to microneedle arrays formed with undercut features for cutaneous and non-cutaneous drug delivery, as well as for tissue adhesive patches.

BACKGROUND

The skin is a readily accessible tissue with many distinct functions such as serving as a protective barrier and a thermal regulator. Remarkably, the skin also functions as an active immune organ. For some purposes, such as immunization, cancer immunotherapy, and allergy desensitization, the skin can be preferred anatomic target site since it harbors large populations of professional antigen-presenting and immune-accessory cells. Most vaccines, immune modifiers, and cancer drugs are administered using hypodermic needle-based injections. However, drug delivery using traditional syringes is associated with several disadvantages. These include requirement for trained healthcare personnel for administration, trypanophobia (i.e., fear of needles), poor patient compliance, risk of disease transmission and needle-stick injuries, and costs of cold chain storage and transport.

In addition, parenteral injections fail to reproducibly and precisely deliver biocargos to targeted skin microenvironments. Thus, vaccines and drugs administered by conventional injections may result in sub-optimal efficacy. Collectively, these factors hinder the effective use of vaccines, cancer drugs, or immunomodulators and lead to inefficient cutaneous immunization and treatment strategies.

SUMMARY

Various methods and systems are disclosed herein relating to the manufacturing of microneedle arrays and, in particular, to microneedle arrays formed with undercut features for cutaneous and non-cutaneous drug delivery, as well as for tissue adhesive patches.

In some of the embodiments described below, a method of forming a microneedle array comprises forming a production mold of a flexible material having plurality of cavities that are shaped to define a plurality of respective microneedles that each have a stem, a microneedle tip, a filleted base, and at least one undercut feature, incorporating at least one bioactive material into a first dissolvable material to provide a biodegradable matrix, delivering the biodegradable matrix into at least the microneedle-tip portion defined by the respective cavities of the production mold, forming a plurality of microneedles in the production mold that include the biodegradable matrix, and removing the microneedles from the production mold by pulling the microneedles out of the mold. The flexible material can have sufficient elasticity to allow for the molded microneedle array to be removed from the production mold in a single pull without damaging the integrity of the shape of the microneedles as defined by the mold.

In other embodiments, a microneedle array is formed using a single-pull mold comprising a backing layer, a plurality of microneedles, and at least one bioactive material combined with a first dissolvable material to form a biodegradable matrix. The plurality of microneedles each have a stem, a microneedle tip, a filleted base, and at least one undercut feature.

In still other embodiments, a method of forming a mold comprises generating a 3D-CAD drawing of a microneedle array that includes a plurality of microneedles with at least one undercut feature, forming a master microneedle array using the 3D-CAD drawing, forming at least one replica of the master microneedle array, and forming a production mold of the microneedle array using the at least one replica. The production mold is formed of a flexible material.

The foregoing and other objects, features, and advantages of the invention will become more apparent from the following detailed description, which proceeds with reference to the accompanying figures.

BRIEF DESCRIPTION OF THE DRAWINGS

FIG. 9A optical microscope images of the PVP/PVA-MNAs incorporating Allura Red dye before human skin application.

FIG. 9B shows bright-field microscope image of Allura Red R40 dye microneedle traces on living human skin samples.

FIG. 9C shows optical microscope images of the PVP/PVA-MNAs incorporating Allura Red dye after human skin application.

FIGS. 9D-I show intradermal co-delivery of Alexa488-labeled Poly(I:C) and Alexa555-labeled OVA from tip-loaded CMC/Treh MNAs. 20× optical magnification. Fluorescence microscope composite images demonstrate delivery cavities penetrating the epidermis and upper dermis, and delivery of both the antigen and adjuvant to targeted skin microenvironments.

FIG. 10A shows an optical microscope images of MNAs integrating both Alexa555-OVA and Alexa488-Poly(I:C), with the fluorescent image being a representative figure of the pyramid head incorporating both cargos.

FIG. 10B shows representative optical microscope images of the Alexa555-OVA and Alexa488-Poly(I:C)-loaded MNAs after an in vivo application to the depicted mouse.

FIGS. 10C and 10D show the effective co-delivery of Alexa488-Poly(I:C) and Alexa555-OVA to the skin microenvironments using novel MNAs.

DETAILED DESCRIPTION

Figure 1:
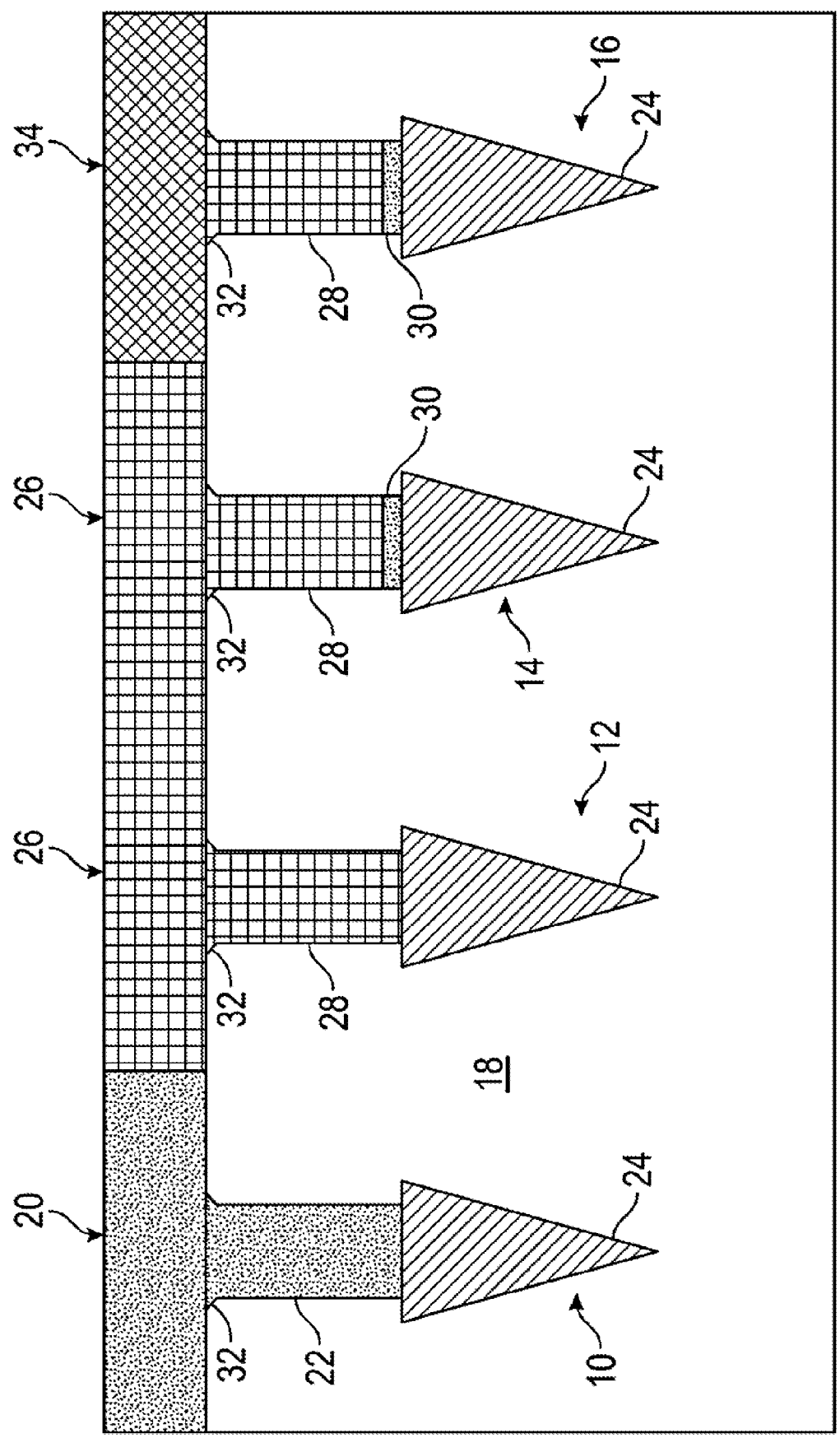
FIG. 1 illustrates exemplary microneedle designs that have, in these examples, sharp-tipped conical heads, circular undercut stems, and filleted bases.

The detailed descriptions herein describe certain exemplary embodiments relating to the manufacture and use of microneedle arrays (MNAs). Although the exemplary embodiments may disclose particular types of MNAs it should be understood that other types of MNAs may benefit from the disclosed systems and methods.

As used herein, the term "biologic," "active component," "biocargo," or "bioactive material" refers to pharmaceutically active agents, such as analgesic agents, anesthetic agents, anti-asthmatic agents, antibiotics, anti-depressant agents, anti-diabetic agents, anti-fungal agents, anti-hypertensive agents, anti-inflammatory agents, anti-neoplastic agents, anxiolytic agents, enzymatically active agents, nucleic acid constructs, immunostimulating agents, immunosuppressive agents, vaccines, and the like. The bioactive material can comprise dissoluble materials, insoluble but dispersible materials, natural or formulated macro, micro and nano particulates, and/or mixtures of two or more of dissoluble, dispersible insoluble materials and natural and/or formulated macro, micro and nano particulates. In this regard, although a number of the MNA examples disclosed herein relate to vaccines and immunizations, any other suitable bioactive material, such as those discussed above, can be used in the novel MNA designs.

As used herein, the term "pre-formed" means that a structure or element is made, constructed, and/or formed into a particular shape or configuration prior to use. Accordingly, the shape or configuration of a pre-formed microneedle array is the shape or configuration of that microneedle array prior to insertion of one or more of the microneedles of the microneedle array into the patient.

As used herein, the term "undercut" or "undercut feature" refers to a recessed surface that is deemed to be inaccessible using standard molding methods and, in particular, to a feature (e.g., an indentation, protrusion, or other geometric shape) that restricts or prevents the withdraw of a molded part having this feature from a conventional one-piece mold.

The systems and methods described herein, and individual components thereof, should not be construed as being limited to the particular uses or systems described herein in any way. Instead, this disclosure is directed toward all novel and non-obvious features and aspects of the various disclosed embodiments, alone and in various combinations and subcombinations with one another. For example, any features or aspects of the disclosed embodiments can be used in various combinations and subcombinations with one another, as will be recognized by an ordinarily skilled artisan in the relevant field(s) in view of the information disclosed herein. In addition, the disclosed systems, methods, and components thereof are not limited to any specific aspect or feature or combinations thereof, nor do the disclosed things and methods require that any one or more specific advantages be present, or problems be solved. Headings are provided solely for purposes of readability and it should be understood that elements and/or steps in one section can be combined with elements and/or steps under different headings in this disclosure.

As used in this application the singular forms "a," "an," and "the" include the plural forms unless the context clearly dictates otherwise. Additionally, the term "includes" means "comprises." Furthermore, as used herein, the term "and/or" means any one item or combination of items in the phrase. In addition, the term "exemplary" means serving as a non-limiting example, instance, or illustration. As used herein, the terms "e.g.," and "for example," introduce a list of one or more non-limiting embodiments, examples, instances, and/or illustrations.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed things and methods can be used in conjunction with other things and methods. Additionally, the description sometimes uses terms like "provide," "produce," "determine," and "select" to describe the disclosed methods. These terms are high-level descriptions of the actual operations that are performed. The actual operations that correspond to these terms will vary depending on the particular implementation and are readily discernible by one of ordinary skill in the art having the benefit of this disclosure.

Exemplary Microneedle Arrays

The use of microneedle arrays has many advantages over conventional needle-based injection techniques. For this reason, cutaneous vaccination or drug delivery using microneedle arrays offers a viable and attractive approach to effective immunization or cancer immunotherapy due to the aforementioned theoretical advantages of the skin.

Unlike topical delivery approaches, MNAs physically penetrate the stratum corneum, thereby eliminating formulation complexities and resulting in localized deposition of vaccines or drugs in the skin microenvironments. In contrast to injections with traditional needles, the microneedles are benign to pain receptors, enabling minimally-invasive pain-free immunization.

Among other benefits, dissolving MNAs can provide highly effective vaccination due to their higher antigen loading capacity, tunable release kinetics, simple manufacturing, and long-term stability. Such MNAs can be created from water-soluble polymers that dissolve when inserted into the skin. The microneedles of MNAs are preferably strong enough in their dry-state to penetrate the stratum corneum, and then rapidly dissolve in the fluid environment of the skin, thereby releasing vaccines. Precise delivery of bioactive materials, such as vaccines, to the cutaneous microenvironments can result in improved efficiencies, thereby requiring relatively lower doses compared to traditional needle injections.

As disclosed in more detail below, microneedles with undercut geometries that include dissolvable and/or non-dissolvable materials can be formed by the novel methods and systems described herein.

In some embodiments, the novel MNAs can be formed via a single-step micromolding process that utilizes flexible production mold materials. The use of such flexible production mold materials allows for the production of a range of geometric designs not otherwise possible. The flexible production mold material can comprise, for example, any elastomer or other flexible material that allows for the removable of the microneedles of a desired design (e.g., a desired amount of undercut and/or other geometric shape). The ability to mold a variety of geometric shapes that are otherwise difficult to manufacture by molding enables novel and innovative functionally-graded MNAs, such as the ones shown in FIG. 1, for targeted delivery of a variety of bioactive materials to skin and other tissues (e.g., cardiac and ocular tissue).

FIG. 1 illustrates examples of different structures of microneedles that can be formed using the methods and systems described herein. Referring to FIG. 1, four different microneedle structures 10, 12, 14, 16 are shown in a production mold 18 that is formed from a flexible material, such as a flexible elastomer.

Microneedle 10 is formed with a dissolvable backing layer 20, a dissolvable stem 22, and a microneedle tip 24 that is loaded with a bioactive material. Thus, microneedle 10 is fabricated from a dissolving (or biodegradable) material throughout. The bioactive material can be mixed into the dissolving material, but is preferably located at the tip of the needles as shown in FIG. 1 to improve delivery efficiency.

As shown in FIG. 1, microneedles 10, 12, 14, 16 can have a pyramid head-shape with a sharp tip and an undercut stem that connects to a backing layer through filleted bases. Fillets 32 can provide improved mechanical performance during tissue insertion.

The MNAs described herein can be fabricated from any moldable dissolving, biodegradable, and/or biocompatible, non-dissolvable materials including carboxymethylcellulose, trehalose, polyvinylpyrrolidone, poly(vinyl alcohol), maltodextrin, silk, glucose, hyaluronic acid, poly(methyl methacrylate), polycarbonate, poly(lactic-co-glycolic acid), poly(lactic acid), light curable resins, and their combinations to incorporate any bioactive materials, including cosmetics, dermal-fillers, statins, growth factors, pain killers, anti-histamines, vitamins, anesthetics, anti-aging agents, small molecule drugs, haptens, allergens, anti-inflammatory agents, proteins, peptides, micro vesicles, exosomes, polyplexes (siRNA, shRNA, DNA vector complexes), recombinant viral vectors (i.e., Adenovirus, Lentivirus, Vaccinia Virus, Adeno-Associated Virus, and their different serotypes), monoclonal and polyclonal antibodies, and live or lysed cells.

Microneedle 12 is formed with a non-dissolvable backing layer 26, a non-dissolvable stem 28, and a microneedle tip 24 that is loaded with a bioactive material. This functionally-graded, undercut MNA design can be fabricated with more than one material. For example, the pyramid portion can be created using a dissolving or biodegradable material, while the stem portion and the backing layer are manufactured from a non-dissolvable material, such as a non-dissolvable biocompatible rigid polymer (e.g., poly(methyl methacrylate), polycarbonate, VeroWhite and other UV-curable and heat curable resins).

Microneedle 12 can, therefore, provide a sharp needle tip along with enhanced mechanical performance through a filleted base enables successful tissue penetration and a pyramid head that serves as the bioactive material dosage form where the bioactive material(s) are incorporated into a dissolving or degrading biomaterial matrix. The undercut stem portion improves the mechanical performance during penetration while ensuring tissue retention during implantation and the non-dissolvable undercut stem portion prevents back diffusion of the embedded bioactive material(s) during both fabrication and implantation processes. The non-dissolvable backing layer can also help prevent absorption of humidity during storage, which may result in excessive curvature of the backing layers and render MNA applications suboptimal.

Microneedle 14 is similar in shape to microneedles 12, 14, but further includes another dissolving layer 30. For example, the pyramid portion is created using a dissolving or biodegradable material and a more quickly dissolving layer is provided adjacent to the stem/needle tip connection. The dissolving layer can be formed for example, from a small molecular weight quickly dissolving polymer such as glucose, sucrose, trehalose, maltodextrin, or polyvinylpyrrolidone. The rest of the stem portion and the backing layer can be formed from a non-dissolvable material, such as a non-dissolvable biocompatible rigid polymer such as acrylated polyesters, epoxies, UV-curable monomers, resins, silicones.

Microneedle 14 therefore provides a sharp needle tip along with enhanced mechanical performance through a filleted base enables successful tissue penetration, a pyramid head that serves as the bioactive material dosage form where the bioactive material(s) are incorporated into a dissolving or degrading biomaterial matrix, an undercut stem portion improves the mechanical performance during penetration while ensuring tissue retention during implantation, and a quickly dissolving layer along with the mechanical mismatch between dissolving and non-dissolving layers that facilitates quick separation of pyramid tips.

Microneedle 16 is similar to microneedle 14 but further comprises a conforming backing layer 34, which may be non-dissolvable. In particular, microneedle 16 can be formed with a pyramid portion that is created using a dissolving or biodegradable material, the quickly dissolving layer can be formed as described above, the rest of the stem portion can be manufactured from a non-dissolvable material, and the backing layer can be manufactured from a conformable material, such as a non-dissolvable conformable polymer (silicones, UV-curable polymers, elastomers).

Microneedle 16 can therefore provide a sharp needle tip along with enhanced mechanical performance through a filleted base enables successful tissue penetration, a pyramid head that serves as the bioactive material dosage form where the bioactive material(s) are incorporated into dissolving or degrading biomaterial matrix, and an undercut stem portion that improves the mechanical performance during penetration while ensuring tissue retention during implantation, As with microneedle 14, the quickly dissolving layer along with the mechanical mismatch between dissolving and non-dissolving layers can facilitate quick separation of pyramid tips and the non-dissolvable undercut stem portion prevents back diffusion of the embedded bioactive material during both fabrication and implantation processes. In this embodiment, the backing layer can conform to non-uniform skin topography better and, if non-dissolvable, it can help prevent absorption of humidity which may result in excessive curvature of the backing layers and render MNA applications suboptimal.

Figure 2A:
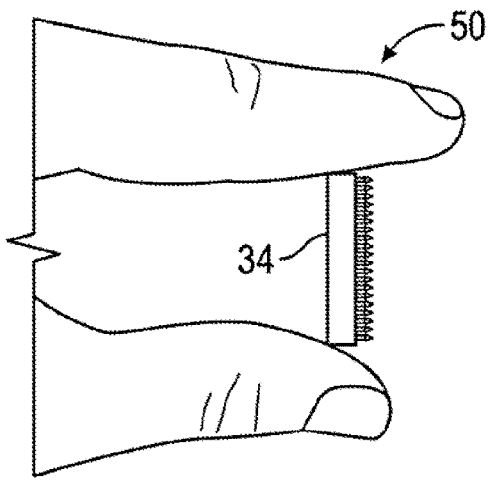
FIGS. 2A-C illustrate a microneedle array that is formed with a conformable backing layer.
Figure 2B:
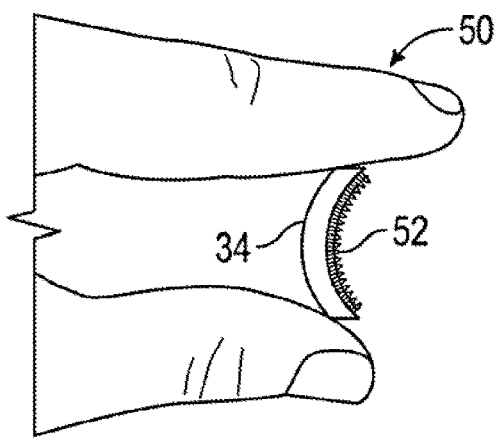
Figure 2C:
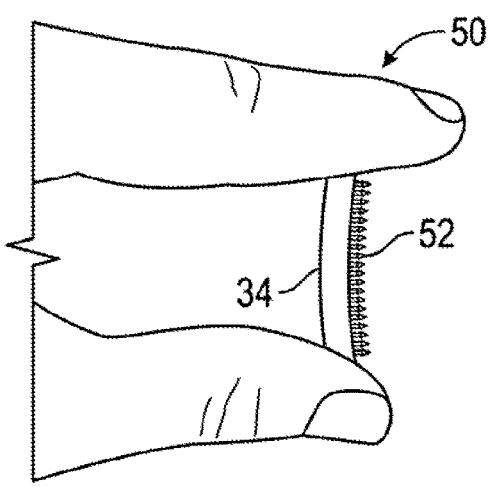

FIG. 2A-2C illustrate the ability of a microneedle array 50 that has microneedles 52 and a conformable backing layer 34 to bend, and after bending return to an original state, or at least a state that is closer in shape to the original state than the bent state.

It should be understood that any combination of the features disclosed in FIG. 1—and throughout this application—is contemplated. For example, the conformable backing layer of microneedle 16 and the quickly dissolving layer 30 of microneedles 14, 16 can be used in combination with any of the other structures disclosed herein (e.g., microneedles 10, 12).

In addition, the processes disclosed herein can be used to create a microneedle that is formed entirely from non-dissolving materials for use as a coated MNAs, tissue adhesives (patches), and/or microbarbs. Non-dissolvable undercut microbarb or microneedle geometries have been created previously using additive manufacturing or mechanical micromachining processes. However, high-throughput manufacturing of those geometries is hindered due to lack of effective micromolding processes.

Micro-Additive Manufacturing of MNAs

In some embodiments, the MNAs can be formed using additive manufacturing (AM), including micro-additive manufacturing (μAM) techniques. The methods and systems described herein can allow medical researchers with little microfabrication expertise to directly produce their MNA designs from a computer-aided design (CAD) drawing without the complex requirements of the subtractive fabrication processes. The μAM techniques described herein provide an effective means for fabrication of novel MNAs designed specifically for effective cutaneous and non-cutaneous drug delivery.

In some embodiments disclosed herein, the MNA designs included uniquely-shaped micron-scale needles that comprising sharp pyramid heads and undercut stems with filleted bases to ensure successful skin penetration and retention. Unlike conventional MNAs, the MNAs disclosed herein are fabricated by a three-dimensional (3D) μAM approach with 3D direct laser writing, which offers transformative potential for the MNA field with its unparalleled level of simplicity and design capabilities.

As described in more detail below, in some embodiments, replicas of the master MNAs can be obtained from a mechanically-strong, moldable resin by a two-step micromolding approach with high fidelity. These replicas can then be used to prepare productions molds, such as polydimethylsiloxane (PDMS) production molds, which enabled fabrication of novel, tip-loaded dissolvable MNAs with undercut microneedles. The resulting MNAs are, in some embodiments, fully-dissolving MNAs with true undercut features for effective cutaneous drug delivery.

As shown in FIG. 1, in some embodiments, a plurality of master MNAs can be printed, replicas of the master MNAs quickly obtained, and then the plurality of replicas can be assembled together to create larger MNAs.

In some embodiments, the MNAs can incorporate a model antigen Ovalbumin (OVA)±a model adjuvant Poly(I:C) from a biodissolvable material composition (70% CMC/ 30% Treh) using a spin-casting method. Furthermore, the proposed MNA designs, along with favorable mold materials, strategically enabled direct fabrication steps without interfering with molding processes. The fabricated MNAs are particularly effective in penetrating through the stratum corneum of living human skin to deliver their biocargos to the cutaneous microenvironments. These unique MNAs fulfill the geometric and mechanical-strength requirements for effective skin penetration for cutaneous vaccination, thereby presenting an alternative promising approach for skin-targeted immunization strategies.

Exemplary Microneedles and Arrays, and Manufacturing Systems Thereof

Figure 3A:
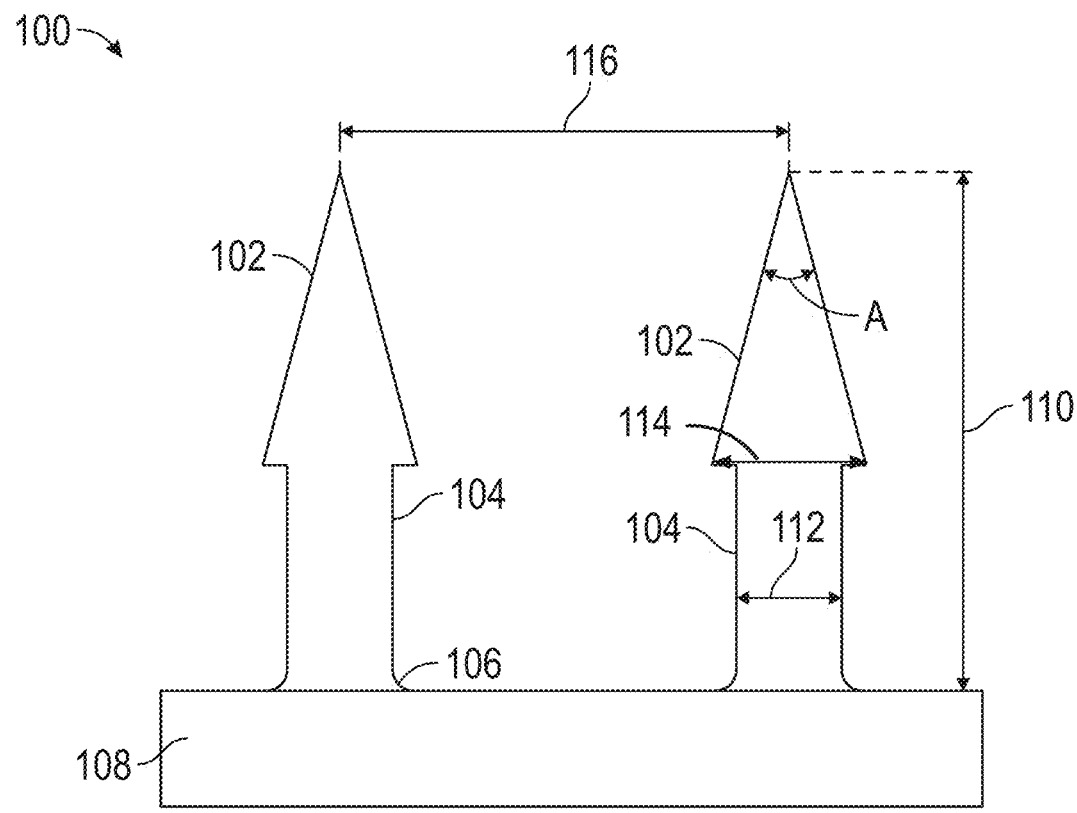
FIG. 3A discloses a computer-aided design (CAD) drawing of an exemplary the MNAs that include sharp needles with undercut features and filleted bases.
Figure 3B:
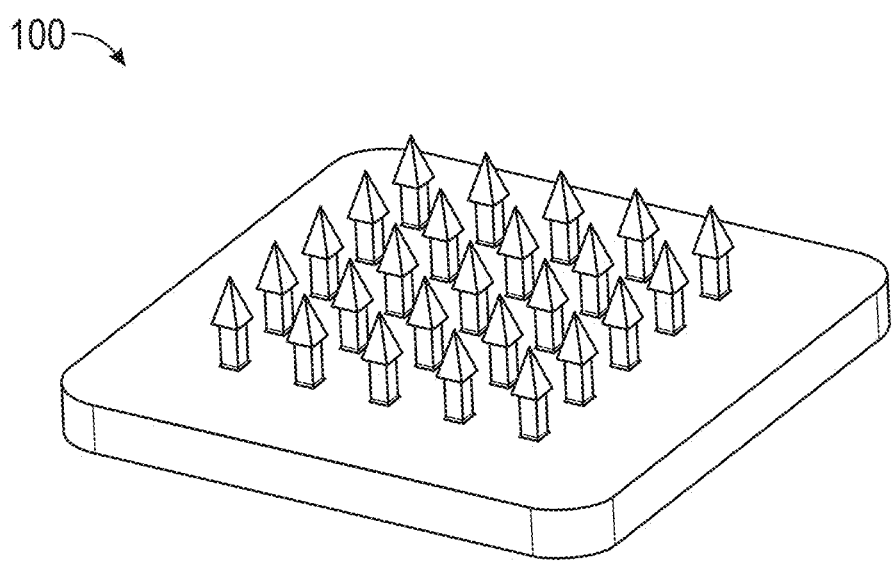
FIG. 3B discloses a 3D CAD drawing of an exemplary MNA with a 5×5 needle arrangement.

FIGS. 3A and 3B illustrate an exemplary microneedle array (MNA) (100) that comprises microneedles with a sharp-tipped pyramid head (102) and an undercut stem portion (104). In addition, the microneedles include a filleted base (106).

The methods and systems disclosed herein enable reproducible fabrication of high-quality, tip-loaded dissolving MNAs with undercut features from different and widely-used dissolving microneedle materials, including CMC, PVP, Silk, HA, CMC/Trehalose, CMC/Glucose, CMC/Sucrose, PVP/PVA, and any other moldable biodissolvable compositions.

In this embodiment, the microneedle has a height (110) that is between 50-1500 μm, such as 750 μm in height, and an apex angle (A) of the pyramid head that is between 10°-60, such as 30°.

In one embodiment, the stem portion of the microneedle can have a width (112) that is between 50-500 μm, such as 150 μm. The stem portion (104) can extend from the bottom region of a three-dimensional (3D) pyramid head to a backing layer (108) of the microneedle with a radius filleted connection that ranged from 15-75 μm, such as 35 μm. A width (114) of the bottom region of the pyramid head can be, for example, between 100-400 μm, such as 250 μm×250 μm base area.

In some embodiments, the tip-to-tip distance (116) between the microneedles in the array can be between 100-800 µm, such as 650 µm. In some embodiments, the MNA can include between 1-1000 microneedles, such as 25 microneedles in a 5×5 array configuration on a backing layer with an area of 4.75 mm×4.75 mm.

The fillet at the microneedle base (106) can help reduce the associated mechanical stress concentrations at sharp corners, and in turn, increases the microneedle performance during manufacturing processes and skin insertion. The apex angle, the width, and the height of the microneedles were selected to provide improved skin insertion mechanics and to reduce failures in penetration.

The undercut, or anchor feature, can improve skin retention during application and, using the novel methods and systems disclosed herein, can be achieved without also interfering with the processing steps, thereby allowing direct removal of the MNAs from the molds.

The three-dimensional micro-additive manufacturing (3D-µAM) approach described herein allows for the creation of unique MNA designs from a 3D-CAD drawing. Furthermore, 3D-µAM can enable medical researchers with little or no microfabrication expertise to design and manufacture MNA-based drug delivery platforms with application-oriented optimizations.

Figure 4A:
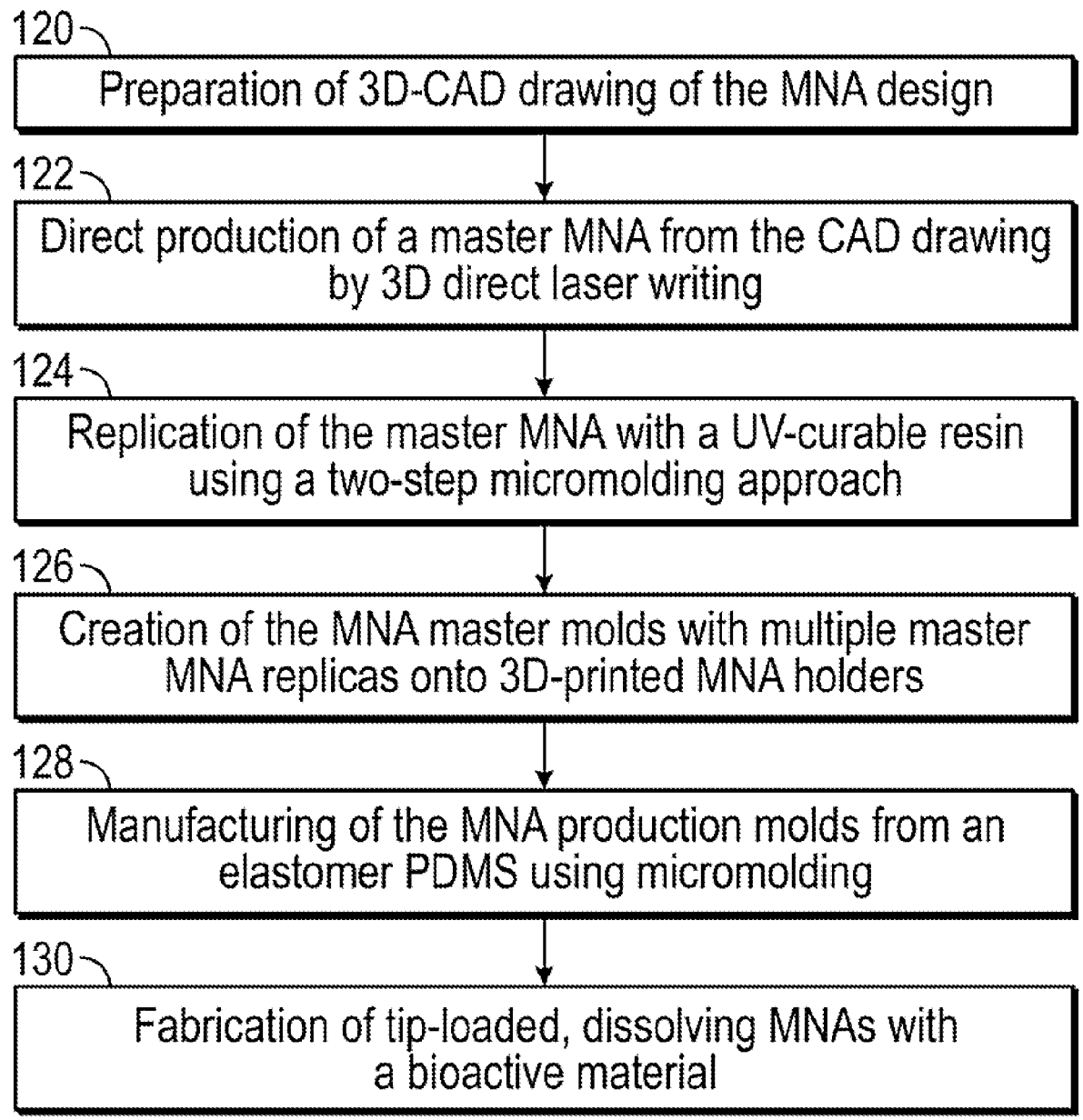
FIG. 4A discloses a flow chart for an exemplary MNA manufacturing process.
Figure 4B:
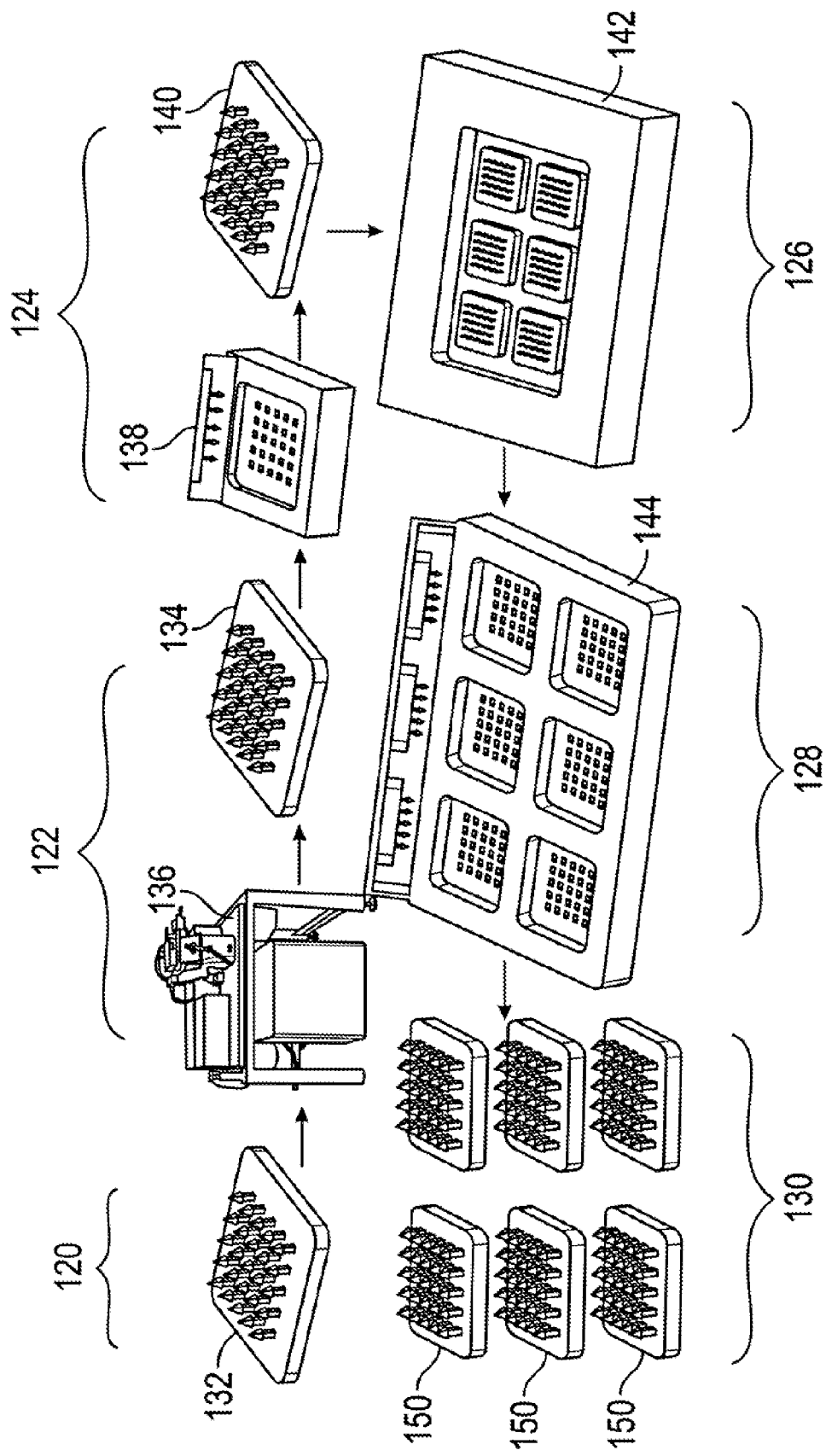
FIG. 4B illustrates the different steps of the exemplary MNA manufacturing process in FIG. 4A.

Exemplary manufacturing systems and processes are presented in a flow chart in FIG. 4A and graphically illustrated in FIG. 4B. As shown in FIGS. 4A and 4B, the process can comprise the following steps to create novel fast-dissolving MNAs while simultaneously achieving high-throughput fabrication. First, a 3D-CAD drawing (132) of the MNA design can be prepared (process step 120). Second, a direct production of the master MNA (134) from the CAD drawing can be produced by 3D direct laser writing using a non-dissolvable resin (e.g., IP-S photoresist) (process step 122). The 3D-µAM manufacturing system can be, for example, a Nanoscribe 3D printing system (136).

Third, a quick and high-fidelity replication of the master MNA can be formed with a UV-curable resin (e.g., VeroWhitePlus, Tangoblack, Digital Materials) using a two-step micromolding approach (process step 124). This approach can include a negative elastomer mold (138) to form the replica (140) of the master MNA.

Fourth, the MNA master molds can be created with multiple master MNA replicas (e.g., six replicas) onto 3D-printed MNA holders (process step 126). The 3D printed MNA holder (142) can be formed of, for example, a resin material. The combination of a plurality of master MNA replicas together onto, for example, 3D-printed MNA holders can allow for the creation of larger MNAs and improve productivity.

Fifth, the MNA production molds (144) can be manufactured from the elastomer PDMS using micromolding (process step 128). Sixth, tip-loaded, dissolving MNAs (150) can be fabricated (process step 130). The MNAs can have undercut microneedles incorporating one or more bioactive material, such as a vaccine or any other bioactive material from a water-soluble biocompatible material (e.g., a composition of CMC and Treh) through a multiple-step spin-casting method using a centrifuge.

For example, a bioactive component (e.g., vaccine) can be spin-casted to the tip of the PDMS production molds and the dissolvable hydrogel (e.g., CMC/Trehalose) can be spin-casted into the production molds to serve as the structural material of microneedles and to form the backing layer of the MNAs. In some embodiments, the master MNA, the MNA master molds including replicas of the master MNA, and the elastomer production molds can be reused for a large number of processing cycles, thereby greatly reducing the fabrication costs for MNAs with unique designs and improving productivity.

Figure 5A:
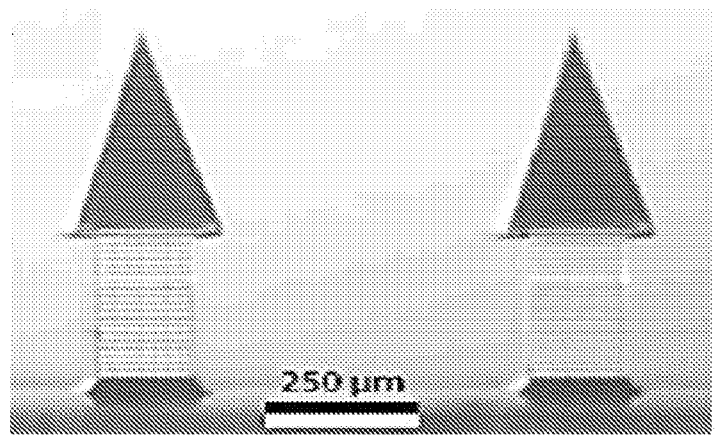
FIG. 5A shows an optical microscope image of a master MNA created using 3D direct laser writing.
Figure 5B:
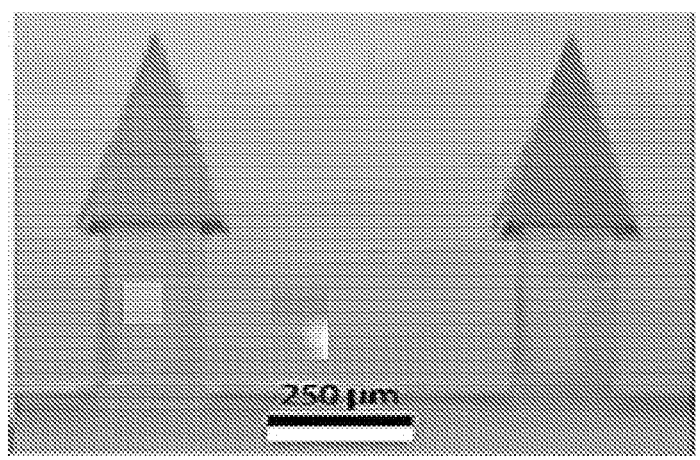
FIG. 5B shows an optical microscope image of the replica of the master MNA created through a two-stage micromolding strategy.
Figure 5C:
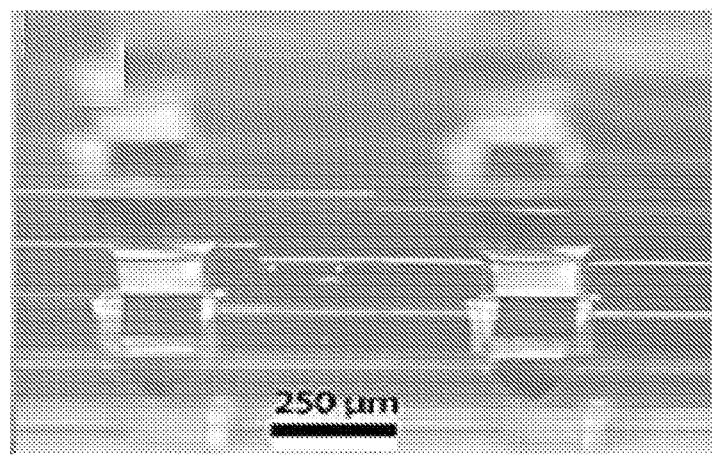
FIG. 5C shows an optical microscope image of the microneedle-shaped wells in MNA production molds.
Figure 5D:
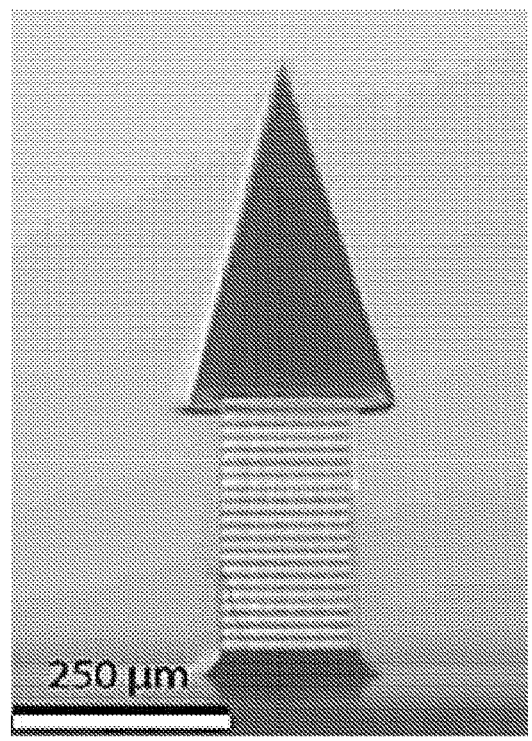
FIG. 5D shows an optical microscope image of an individual undercut needle on the 3D printed master MNA.

FIGS. 5A-5E show final products corresponding to different manufacturing or processing steps. FIG. 5A shows an optical microscope image of the master MNA (134) created using 3D direct laser writing and FIG. 5D shows an optical microscope image of an individual undercut needle on the 3D printed master MNA (134). Specifically, the master MNA was fabricated from IP-S photoresist by 3D direct laser writing. IP-S is a specific material designed for 3D laser lithography and provides high resolution and mechanical integrity for micro- and nano-structures. 3D laser lithography based on two-photon polymerization provided an effective means for fabrication of undercut MNA designs with smooth edges and sharp tips, and without any unwanted residues (e.g., machining chips).

Figure 5E:
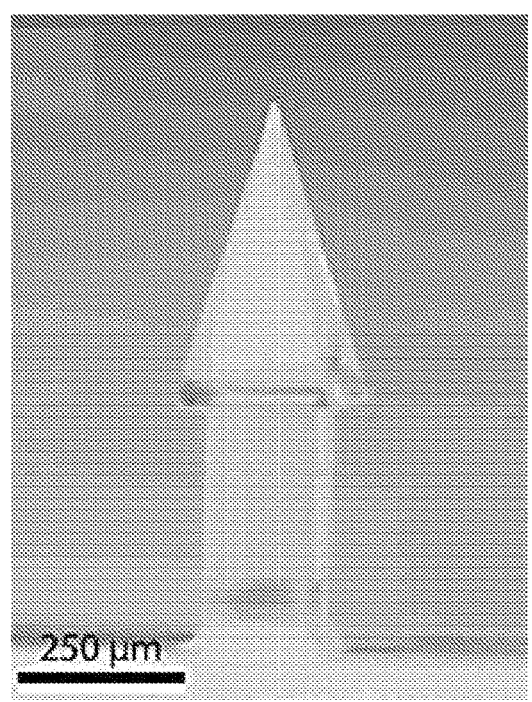
FIG. 5E shows an optical microscope image of an individual undercut needle on the replica of a master MNA.

FIG. 5B shows an optical microscope image of the replica (140) of the master MNA created through a two-stage micromolding strategy: elastomer molding combined with UV-curable micromolding and FIG. 5E shows an optical microscope image of an individual undercut needle on the replica (140) of the master MNA. The master MNA was produced using a two-step micromolding process. The IP-S master MNA was used to fabricate PDMS flexible mold through elastomer molding and then the PDMS mold was used to manufacture several VeroWhite MNA replicas through UV-curable micromolding. VeroWhite resin is a wear-resistant, acrylic-based photo-polymer that can be used with 3D Polyjet printers.

To achieve scalable manufacturing of novel MNAs, the MNA replicas were then used to create MNA master molds that include a number of MNAs (e.g., six MNA replicas). The final MNA master molds were post-processed in a vacuum oven to facilitate successful curing of PDMS on the mold surface and then the elastomer MNA production molds, which consisted of microneedle-shaped wells, were fabricated from PDMS. FIG. 5C shows an optical microscope image of the microneedle-shaped wells in MNA production molds (144).

As such, these processing steps, along with high geometric capability of 3D direct laser writing, resulted in a scalable and effective MNA manufacturing strategy. Furthermore, rapid replication of the 3D printed master MNA using a wear-resistant moldable material improved productivity substantially. Other undercut features using different microneedle and elastomer mold materials, consistent with the processes and systems described herein, are also possible.

Upon fabrication of the MNA master molds with six MNA replicas, dissolving MNAs that integrate the vaccine in the tip portion of the needles were fabricated using the conventional three-stage manufacturing strategy through master mold to production mold to final dissolvable MNAs.

As discussed in more detail below, dissolving MNAs that incorporated the vaccine (10 µg OVA±25 µg Poly(I:C)) in the tip portion of the undercut needles were fabricated through the spin-casting process from two different material compositions (i.e., CMC/Trehalose and PVP/PVA). Furthermore, tip-loaded CMC/Trehalose MNAs with undercut microneedles integrating a colored model drug (e.g., Doxorubicin) were fabricated to facilitate imaging and demonstrate compatibility with chemotherapeutic agents. The systems and methods described herein enabled effective and rapid fabrication of tip-loaded dissolving MNAs with undercut microneedles from different dissolvable material compositions.

Figure 6A:
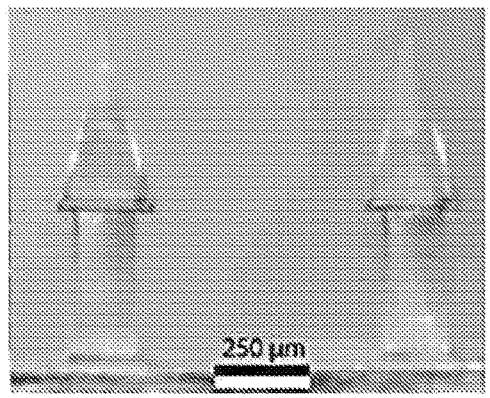
FIG. 6A shows an optical microscope image of final dissolving (CMC/Treh) MNAs incorporating biocargos (e.g., OVA+Poly(I:C)).
Figure 6B:
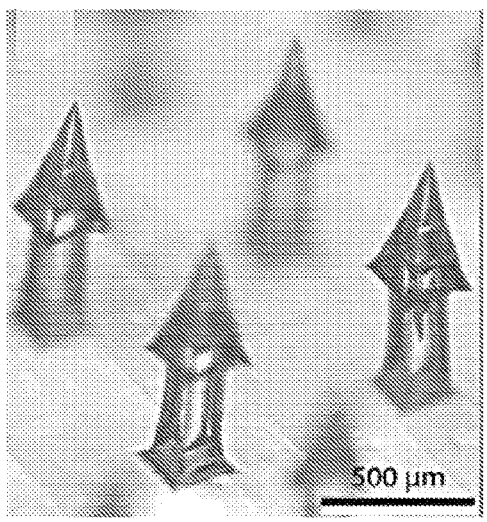
FIG. 6B shows an optical microscope image of dissolving, tip-loaded PVP/PVA MNAs with undercut microneedles integrating OVA.
Figure 6C:
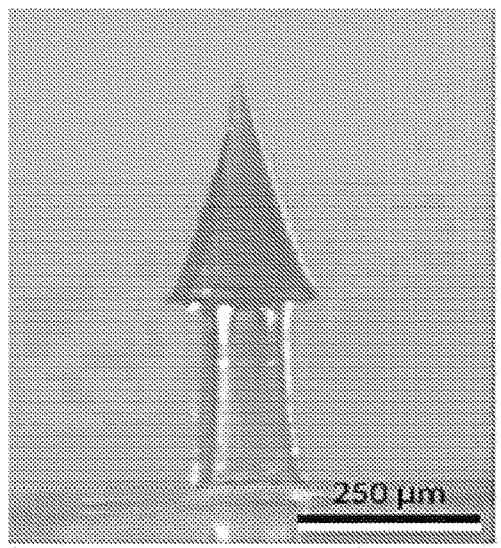
FIG. 6C shows an optical microscope image of an individual tip-loaded CMC/Treh undercut microneedle incorporating Doxorubicin as a colored drug to facilitate imaging.

FIG. 6A shows an optical microscope image of final dissolving (CMC/Treh) MNAs incorporating biocargos (e.g., OVA+Poly(I:C)). FIG. 4B shows an optical microscope image of dissolving, tip-loaded PVP/PVA MNAs with undercut microneedles integrating OVA, and FIG. 4C shows an optical microscope image of an individual tip-loaded CMC/Treh undercut microneedle incorporating Doxorubicin as a colored drug to facilitate imaging.

Example 1—Manufacturing of Exemplary MNAs

An exemplary process for creating an MNA is described herein.

Fabrication of master MNA. A unique MNA design was directly created from the 3D-CAD drawing shown in FIG. 1 using 3D laser printing (Nanoscribe Photonic Professional, GT) with the photopolymetric resist IP-S. The Nanoscribe printing system was equipped with a laser generator, an optical cabinet, a Zeiss optical microscope attached to a lens to focus the laser beam, a Galvo mirror system to direct the laser-beam scanning, a piezoelectric stage for precise motion control, and an operation software (Nanowrite) to execute 3D printing. The whole system was placed on an optical table to eliminate vibrations during the printing process.

To fabricate the master MNA, the MNA design was converted into 'STL' (StereoLithography) format. Subsequently, the STL file was loaded into the specialized software (DeScribe, Germany) of the Nanoscribe system to select the processing conditions (i.e., the distance of slicing, hatching, and splitting). Finally, the STL file was converted into 'GWL' (General Writing Lithography) format to be exported in the Nanowrite software for printing the master MNA. The master MNA was fabricated using Galvo-scan mode in XY plane and piezo-scan mode in Z direction. The master MNA was split into blocks of 220 μm×220 μm×200 μm within the working range and then stitched together. The laser power and writing speed was set to be 100 mW and 6 cm/s, respectively. The minimum and maximum slicing distances of 0.3 μm and 0.5 μm, respectively, were used. The master MNA was then printed through two-photon polymerization of the IP-S photoresist by a femtosecond pulsed laser at a wavelength of 750 nm using a unique deep-in-liquid mode with the objective of 25× and NA0.8 in Shell and Scaffold mode.

After printing, the master MNA was developed in the photoresist solvent propylene glycol monomethyl ether acetate (PGMEA) for 30 min, followed by 5 min isopropyl alcohol (IPA) rinse. After the master MNA was dried in the air, it was placed under a UV (365 nm) light with 16 mW/cm2 intensity for 30 min to further crosslink the body to strengthen the MNA structure.

Replication of master MNA. To replicate the master MNA with high-fidelity using a UV-curable resin, a two-stage micromolding method was performed. First, an elastomer mold which is negative of the master MNA was manufactured from polydimethylsiloxane (PDMS) using a micromolding approach. Elastomer molding using PDMS provides an accurate and reproducible replication of high-fidelity micron-scale structures. Briefly, the master MNA was mounted in a petri-dish with a diameter of 5 cm and PDMS was obtained using the two-component curable silicone elastomer, SYLGARD® 184 (Dow Corning), by mixing the base material with a curing agent in 10:1 SYLGARD®-to-curing agent ratio. Subsequently, the mixture was poured over the master MNA mounted into the petri-dish and degassed for 15 min Next, the master MNA with the degassed mixture was placed in an oven and cured at 70° C. for 1 h. The cured PDMS was cooled down to room temperature for 5 min and then separated from the master MNA to obtain the negative PDMS mold.

The second processing step used the negative PDMS mold for fabrication of positive MNA replicas from the UV-curable resin (Stratasys®, VeroWhiteplus-RGD835). For each PDMS mold, 20 μl of liquid (uncured) resin was poured onto the molds and then the molds were placed in a centrifuge to fill the microneedle-shaped wells with the resin at 4500 RPM and at 20° C. for 1 min. The resin was then cured under UV light (365 nm) with 21.7 mW/cm2 intensity for 5 min from each of the top and bottom sides to cure both the base and the microneedle tips. To ensure that the backing layers of the replicas of the master MNA were flat, a secondary loading of 50 μl UV-curable resin onto the PDMS mold was performed, which was excess to the remaining volume available. A glass slide was placed on top of the mold to get rid of the excess VeroWhite resin, thereby creating a uniform flat surface at the base. The liquid resin was then cured from the top side for 5 min, and then demolded to obtain the replicas of the master MNA.

Creation of MNA master molds. To facilitate scalable manufacturing of dissolving MNAs, the MNA master molds were created through assembling six replicas of the master MNA onto the MNA holders fabricated by Stratasys® from a non-dissolvable photo-polymer (VeroWhite) using a high-resolution (16 μm) Polyjet 3D printing system (Objet Connex 500 multi-material). The 3D model of the MNA holders created using SolidWorks 2018 CAD software and then converted into the 'STL' (StereoLithography) file format. Subsequently, the specialized software (Objet Studio) sliced this 3D model into 2D cross-sectional layers, creating a computer file that was sent to the 3D printer system. The channels in the 3D printed MNA holder were designed and fabricated to serve as raised pockets in the MNA production molds to assist as reservoirs for both the bioactive cargo (e.g., vaccine) and the structural hydrogel material of dissolving MNAs during the spin-casting process. The created MNA master molds were baked at 80° C. overnight in a vacuum oven to facilitate effective fabrication of elastomer MNA production molds.

Manufacturing of MNA production molds. The MNA production molds that included microneedle-shaped wells were fabricated from a commonly-used elastomer polydimethylsiloxane (PDMS) as described for the replication of the MNA master. The base material was mixed with a curing agent in 10:1 SYLGARD®-to-curing agent ratio. Subsequently, the mixture was poured over the MNA master mold placed in a 10 cm diameter petri-dish and degassed for 15 min. Next, the master mold with the degassed mixture was placed in an oven to cure PDMS at 70° C. for 1 h. After cooling down the cured PDMS to room temperature, it was separated from the MNA master mold to fabricate the PDMS MNA production molds.

Production of dissolving MNAs. To fabricate tip-loaded, dissolving MNAs with undercut microneedles incorporating OVA±Poly(I:C), a biodissolvable material composition that included carboxymethylcellulose (CMC, cat #C5678, Sigma-Aldrich, St Louis, MO) and trehalose (Treh, Cat #T9531, Sigma-Aldrich) was used. To prepare the hydrogel form of the structural material of dissolving MNAs, the CMC and Treh powders were thoroughly mixed based on the weight ratio of 70% and 30%, respectively. This powder mixture was then added to endotoxin-free water (HyClone HyPure Cell Culture Grade Water) and thoroughly mixed to achieve a 30% w/w solute concentration. The prepared hydrogel was refrigerated at 4° C. for 24 h for the mixture to equilibrate. Tip-loaded CMC/Treh-MNAs with the unique designs were then manufactured through a multiple-step spin-casting technique using a centrifuge (Thermo Fisher Scientific Sorvall Legend XTR with Swinging Bucket Rotor TX-750).

First, 5 µL of OVA solution (25 mg/mL OVA in endotoxin-free water) was dispensed over each of the MNA on the PDMS production molds, and the production molds were centrifuged for 1 min at 20° C. and at 4500 rpm to fill the microneedle-shaped cavities. Once the production molds were filled, the excess OVA solution within the reservoir was recovered. The production molds were again centrifuged for 30 min at 20° C. and at 4500 rpm to ensure that dry OVA cargo was located at the tip portion of the needle-shaped cavities in the production molds.

For MNAs integrating OVA+Poly(I:C), after loading OVA, 5 µL of Poly(I:C) solution (62.5 mg/mL Poly(I:C) in endotoxin-free water) was dispensed over each of the MNA on the PDMS production molds, and the production molds were centrifuged for 1 min at 20° C. and at 4500 rpm to fill the microneedle-shaped cavities. Once the production molds were filled, the excess Poly(I:C) solution within the reservoir was recovered. The production molds were again centrifuged for 30 min at 20° C. and at 4500 rpm to ensure that Poly(I:C) cargo was also located at the pyramid portion of the needle-shaped cavities in the production molds. After locating the biocargos at the tip of microneedles, 40 µL of hydrogel (30% w/w 70:30 CMC:Treh) was loaded over each of the MNAs on the PDMS production molds to fill the microneedle-shaped geometries in the production molds and to form the backing layers of the MNAs. The hydrogel-loaded production molds were then centrifuged for 5 h at 20° C. and at 4500 rpm to obtain dissolving MNAs loaded with 10 µg OVA±25 µg Poly(I:C). Due to the specific geometry of the MNA production molds, each replication produced six arrays of OVA±Poly(I:C)-loaded dissolving MNAs simultaneously.

To demonstrate fabrication of dissolving MNAs with undercut microneedles from another water-soluble material (i.e., material capability), a biodissolvable polymer composition of Polyvinylpyrrolidone (PVP) and Polyvinyl alcohol (PVA) (40% w/w 60:40 PVP:PVA) was also used to fabricate MNAs with different biocargos. The fabricated master MNAs, replicas of MNAs, elastomer MNA production molds, and OVA±Poly(I:C)-loaded dissolving MNAs were imaged using bright-field optical microscopy to assess geometric integrity of the novel microneedles with undercut features.

Cutaneous Delivery Using Exemplary MNAs

Preparation of ex vivo human skin explants. Human skin explants were prepared from deidentified healthy donors undergoing plastic surgery acquired through the Pitt Biospecimen Core and used according to University of Pittsburgh Medical Center guidelines. Tissue was rinsed in 70% ethanol and then in phosphate-buffered saline (PBS). Human skin explants (approximately 1 mm thick) were harvested using a Silver's miniature skin graft knife (Padgett, Integra Miltex, Plainsboro, NJ), and then cut into 20 mm×20 mm square pieces. The resulting human skin samples were comprised of unaltered epidermis and a thin layer of underlying dermis, and maintained as explants in normal physiological state by culture at an air-fluid interface.

Imaging analysis. To evaluate MNA-directed intradermal bioactive materials (e.g., vaccine) delivery to living human skin explants, a number of imaging analyses was performed. Tip-loaded CMC/Treh-MNAs integrating a colored cargo (i.e., Allura Red R40 dye) were fabricated using the manufacturing strategy described above. Prior to application of MNAs to the human skin explants, MNAs were imaged using bright-field optical microscopy.

Subsequently, MNAs were applied to human skin explants and removed after 10 min. The targeted human skin regions were then examined under a bright-field microscope to image the patterns of the colored biocargo deposited from CMC/Treh-MNAs into the human skin. Remaining MNA materials were also imaged using optical microscopy after human skin applications. For further qualitative assessment of MNA-directed intradermal vaccine delivery to human skin, CMC/Treh MNAs that incorporate both Alexa555-labeled OVA and Alexa488-labeled Poly(I:C) were fabricated, applied to human skin for 10 min, and removed. The targeted human skin explants were then histologically analyzed. Briefly, the MNA-treated human skin samples were fixed in 2% paraformaldehyde followed by immersion in sucrose solution, with 3 changes of this solution over 24 h. Tissue sections were then flash frozen in optimum cutting temperature (OCT) histology compound, and cryo-sectioned into approximately 10 µm thick sections. The sectioned human skin samples were counter-stained using nuclear DAPI fluorescent dye. The stained sections were then imaged using a Nikon transmission fluorescent microscope to detect Alexa555-OVA and Alexa488-Poly(I:C) into the cross-sections of human skin, as well as using bright field microscope to better demonstrate the stratum corneum breaching.

MNA-Directed Skin Immunization In Vivo.

Mice and animal husbandry. Female C57BL/6J mice were purchased from The Jackson Laboratory (Bar Harbor, ME) and used at 8-10 weeks of age. Mice were maintained under specific pathogen-free conditions at the University of Pittsburgh, and all experiments were conducted in accordance with the institutional animal care and use committee (IACUC) guidelines.

In vivo IVIS imaging. In vivo intradermal vaccine delivery using novel dissolving MNAs was demonstrated using a C57BL/6J mouse. Tip-loaded CMC/Treh-MNAs integrating both Alexa555-labeled OVA and Alexa488-labeled Poly(I:C) were created using the manufacturing strategy described above and applied to the abdomen of the mouse that was temporarily anaesthetized via isoflurane inhalation for 10 min Next, MNAs were removed and the mouse was returned to their normal activity. OVA+Poly(I:C) loaded MNAs were imaged before and after in vivo application Imaging of the MNA-treated mouse was performed on the IVIS 200 in vivo imaging system (PerkinElmer) using the filters to assay for fluorescent-labeled Poly(I:C) and OVA the MNA application site. The image was post-processed using Living Image software (PerkinElmer).

Cell-mediated and humoral immune responses. To demonstrate cutaneous vaccination with novel MNAs, tip-loaded CMC/Treh MNAs integrating 10 µg OVA±25 µg Poly(I:C) were prepared as described above. Mice were immunized by cutaneous vaccination using MNAs (10 µg OVA±25 µg Poly(I:C) MNAs applied to the right and left sides of abdomen, two MNAs per mouse) or by two intramuscular injections of 10 µg OVA in PBS into hind limb gastrocnemius muscle or left untreated (i.e., naïve) Immunizations were performed at days 0 and 7 as prime and boost doses, respectively. Mice were then assayed for in vivo OVA-specific cytotoxic-T-cell activity, and OVA-specific antibody response 5 days after the boosting dose using well-established techniques.

For OVA-specific antibody response, blood was collected from anesthetized mice at the time of sacrifice by cardiac puncture, and serum was isolated using BD Microtainer serum separator tubes (BD Biosciences, San Jose, CA). OVA-specific IgG1 and IgG2c antibodies in serum were measured by indirect ELISAs. Costar EIA/RIA plates (Corning Inc., Corning, NY) were coated with OVA (100 µg/mL in 0.5 M carbonate-bicarbonate buffer, pH 9.6; Sigma) by overnight incubation at 4° C. Plates were washed (3×) with 0.05% Tween20 in PBS, and blocked with 1% goat serum in PBS for 1 hour at 37° C. Serum samples and standards (anti-OVA IgG1 from Cayman Chemical, Ann Arbor, MI; anti-OVA IgG2c from Chondrex, Redmond, WA) were diluted with 1% goat serum, added to plates, and incubated 2 hours at 37° C. After washing (3×), plates were incubated for 1 hour at 37° C. with biotinylated secondary antibodies (goat anti-mouse IgG1 or IgG2c, 1:20,000 in 1% goat serum; Jackson ImmunoResearch, West Grove, PA). Plates were then washed (3×) and incubated for 30 min with streptavidin-HRP (1:1000 in 1% goat serum; BD Biosciences). Plates were washed (3×) again and incubated at room temperature with 4,4',5,5'-tetramethylbenzidine (TMB) peroxidase substrate (Sigma) for 2-3 minutes, and the reaction quenched with 1.0 M H2SO4. For all ELISAs, absorbance at 450 nm (OD450) was read with a SpectraMax 340PC plate reader (Molecular Devices, Sunnyvale, CA), and serum concentrations calculated from standard curves.

To assess OVA-specific cytotoxic T-cell (CTL) activity, splenocytes from naïve mice were pulsed with 2 µg/ml OVA257-264 (SIINFEKL) peptide, or left unpulsed for 1 h. Antigen pulsed splenocytes were washed and stained with high concentration carboxyfluorescein succinimidyl ester (CFSE, 10 µM), while unpulsed splenocytes were labeled with low concentration CFSE (1 µM) for 15 min at 37° C. A 1:1 mixture of pulsed target cells and unpulsed control cells (107 each) was intravenously (IV) injected into immunized and naïve mice. Twenty hours after adoptive transfer, spleens of mice were isolated, and killing of target cells was evaluated by comparison of the antigen pulsed and unpulsed populations by flow cytometry to quantify OVA-specific killing of the high CFSE labeled SIINFEKL-pulsed targets. Specific lysis was calculated and expressed as a percentage of maximum lysis as % Lysis={1−[(mean CFSElow/CFSEhigh ratio from naïve mice)/(CFSElow/CFSEhigh ratio from vaccinated mouse)]}×100.

Intradermal and Non-Cutaneous Uses

Figure 7A:
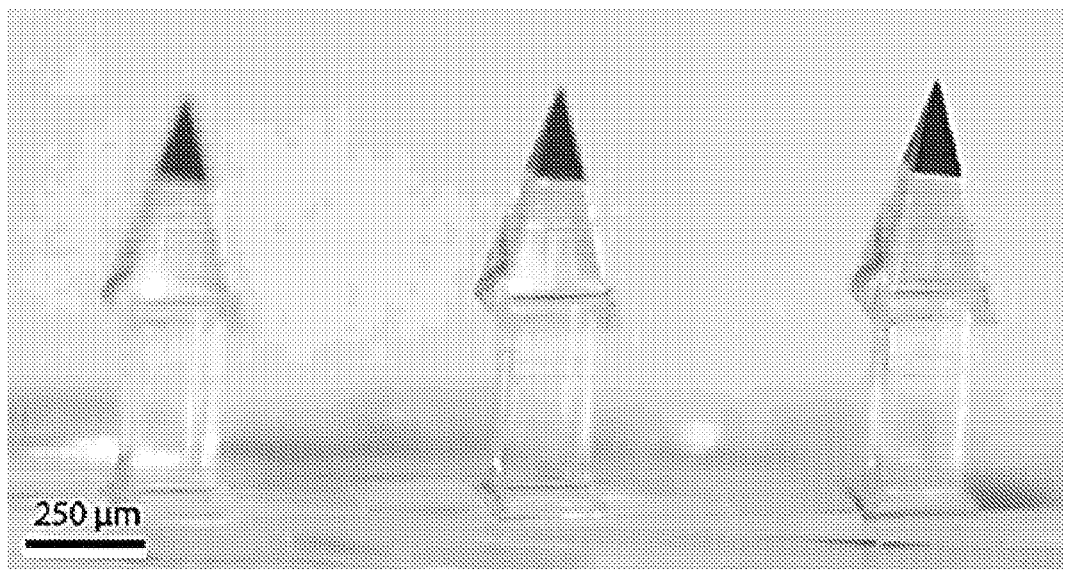
FIG. 7A shows PVP/PVA MNAs incorporating Texas Red labeled Dextran (approximately 40 kDa molecular weight) at the tips of microneedles.
Figure 7B:
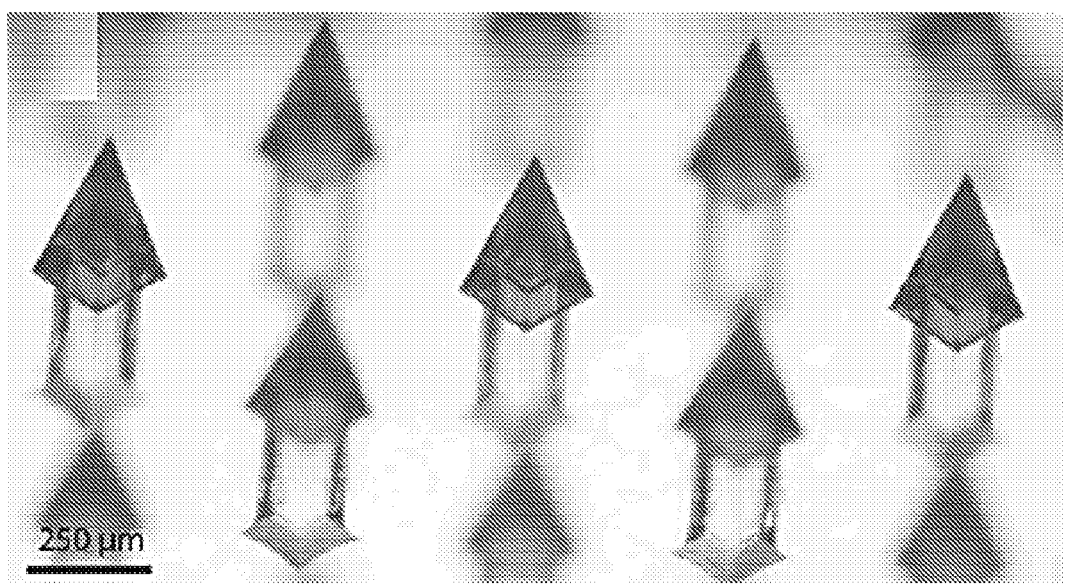
FIG. 7B shows tip-loaded CMC/Treh MNAs integrating Allura Red R40 dye (approximately 500 Da molecular weight) at the pyramid region of microneedles.

In addition to cutaneous vaccination, the MNAs described herein can be used for a broad range of intradermal and non-cutaneous (e.g., ocular and cardiac tissues) drug delivery applications. As shown in FIGS. 7A-D, the biocargo of interest can be located at the very tip of microneedles in the spin-casting process (i.e., a portion of a pyramid) or the entire pyramid region can be loaded with the biocargo depending on the dose requirements. FIG. 7A shows PVP/PVA MNAs incorporating Texas Red labeled Dextran (approximately 40 kDa molecular weight) at the tips of microneedles, while FIG. 7B shows tip-loaded CMC/Treh MNAs integrating Allura Red R40 dye (approximately 500 Da molecular weight) at the pyramid region of microneedles.

Figure 7C:
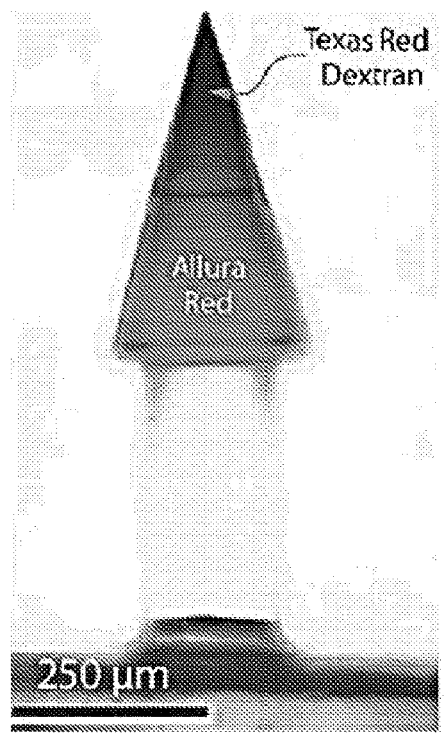
FIG. 7C shows tip-loaded PVP/PVA MNAs incorporating multiple cargos such as Texas Red labeled Dextran and Allura Red R40 dye.
Figure 7D:
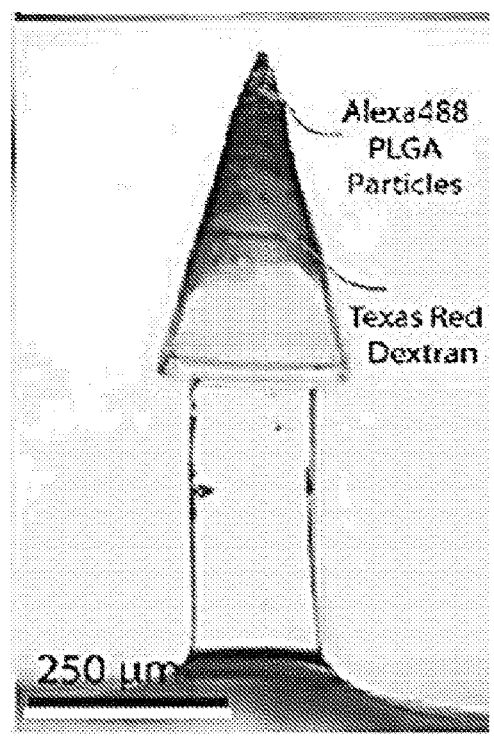
FIG. 7D shows tip-loaded PVP/PVA MNAs incorporating multiple cargos such as Texas Red-labeled Dextran and Alexa488-labeled PLGA microparticles (10 μm mean diameter).

Furthermore, a number of repeated spin-casting steps can be performed to fabricate high-quality MNAs with undercut microneedles that incorporate multiple cargos in their pyramid regions (FIGS. 7C and 7D). FIG. 7C shows tip-loaded PVP/PVA MNAs incorporating multiple cargos such as Texas Red labeled Dextran and Allura Red R40 dye, and FIG. 7D shows tip-loaded PVP/PVA MNAs incorporating multiple cargos such as Texas Red-labeled Dextran and Alexa488-labeled PLGA microparticles (10 µm mean diameter).

As such, the presented approach and novel MNA designs are compatible with single and combination therapies for several cutaneous and non-cutaneous applications. Importantly, the same production molds can be used to effectively fabricate dissolving MNAs with undercut microneedles for several cycles (e.g., FIGS. 7A and 7C show the MNAs obtained after the first and twelfth cycles using t, respectively). Most importantly, in vivo cutaneous vaccination applications of the single (OVA)– and multiple-cargo(OVA+ Poly(I:C)) MNAs were demonstrated in the current study.

Additive manufacturing or 3D printing, as used in the systems and methods described herein provides for accurate and reproducible manufacturing of 3D complex geometries without design limitations and offers a high degree of design flexibility and control. Using the systems and methods here, rapid design-to-fabrication turnaround for optimal application-driven drug delivery systems is possible.

Diverse Needle Geometries

As discussed above, the systems and methods disclosed herein offer an unprecedented level of design flexibility for MNA designs. To demonstrate the range of geometric capability of 3D direct laser writing, microneedle designs were fabricated with diverse geometries.

Figure 8A:
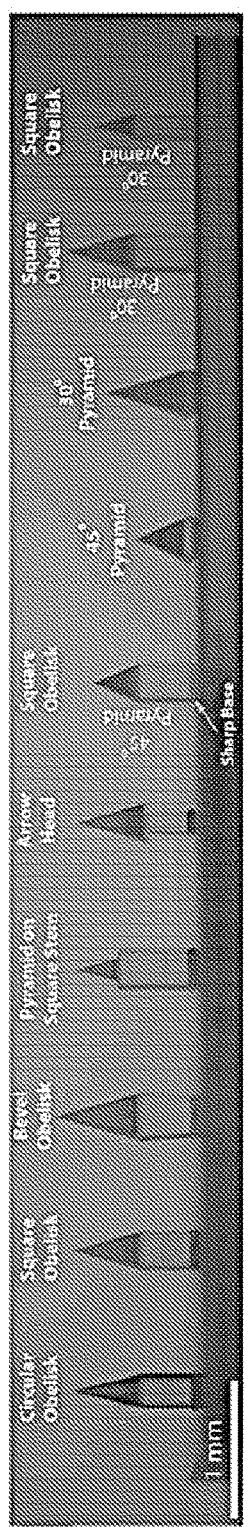
FIG. 8A illustrates different microneedle designs fabricated from IP-S photoresist using 3D direct laser writing.
Figure 8B:
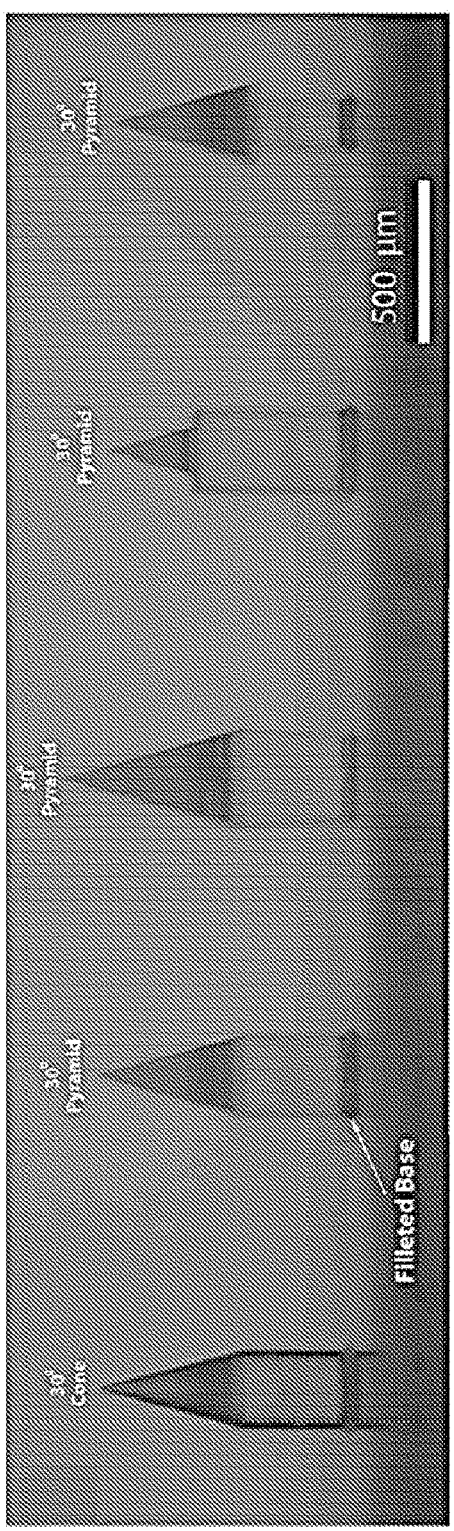
FIG. 8B illustrates images of printed microneedles with filleted bases.

FIGS. 8A-8B show that this technology enables fabrication of a wide range of microneedle geometries with high-fidelity towards application-driven optimization. Furthermore, as shown in FIGS. 8A-8B, it allows a wide range of design changes, including height, width, apex angle, and geometry of the microneedles without requiring complex and custom processing steps. As such, this technology paves the way for design and fabrication of application-driven unique MNA designs.

MNA-Based Intradermal Vaccine Delivery to Human Skin

To evaluate cutaneous biocargo delivery characteristics of novel MNAs with undercut needles, MNAs tip-loaded with Allura Red R40 dye were manufactured using the presented fabrication strategy. Human skin explants were prepared as described above. Allura Red R40 dye loaded MNAs were applied to living human skin explants and removed after 10 min Images of these MNAs before (FIG. 9A) and after (FIG. 9B) application demonstrated high-quality MNAs and the complete dissolution of the microneedles, respectively. The corresponding deposits of MNA-embedded cargo (e.g., Allura Red R40 dye) in the targeted skin was shown in FIG. 9C.

Successful vaccine delivery through the stratum corneum into the immune cell-rich cutaneous microenvironments is critical for effective intradermal immunization. To anatomically evaluate the delivery of OVA and Poly(I:C) into human skin, CMC/Treh MNAs incorporating both Alexa555-labeled OVA and Alexa488-labeled Poly(I:C) were applied to human skin explants for 10 min and then removed. The targeted human skin was cryo-sectioned and imaged using a Nikon transmission fluorescent microscope. Histology demonstrated microneedle cavities penetrating through the epidermis into the dermis (FIG. 9G), and delivery of fluorescent labeled OVA and Poly(I:C) to targeted human skin microenvironments (FIG. 9D-I: DAPI nuclear stain, Alexa488-labeled Poly(I:C), Alexa555-labeled OVA, Brightfield, overlay of 3 different fluorescent colors, merged image of all the fluorescent images with the brightfield image, respectively). In FIGS. 9D-I, the scale bars correspond to 100 µm.

Together, these images suggest that the presented unique MNAs fulfilled the geometric (i.e., sharp tips and smooth edges) and mechanical-strength requirements for failure-free human skin penetration (i.e., breaching through the stratum corneum and viable epidermis) and material requirements for efficient dissolution in the aqueous environment of the skin, thereby presenting an effective cutaneous drug and vaccine delivery platform.

MNA-Directed Cutaneous Immunization In Vivo

To study intradermal vaccine delivery using novel MNAs in vivo in mice, CMC/Treh MNAs with high-fidelity undercut microneedles incorporating both Alexa555-labeled OVA and Alexa488-labeled Poly(I:C) were fabricated as described above. Prior to application, Alexa555-OVA+Alexa488-Poly(I:C) MNAs were imaged using bright-field optical microscopy and epi-fluorescent microscopy (FIG. 10A). MNAs were then applied to mice and removed after 10 min. The remaining MNA material after applications was also imaged using bright-field optical microscopy (FIG. 10B). MNA-treated mice were imaged using the IVIS 200 live animal imaging system with filters for both Alexa488-Poly(I:C) and Alexa555-OVA. MNA-directed co-delivery of Poly(I:C) and OVA were shown in FIGS. 10C and 10D, respectively. Together, these images demonstrated successful application of novel MNAs in vivo in mice, and in turn, MNA-directed effective cutaneous drug and vaccine delivery with new MNA designs.

Figure 11A:
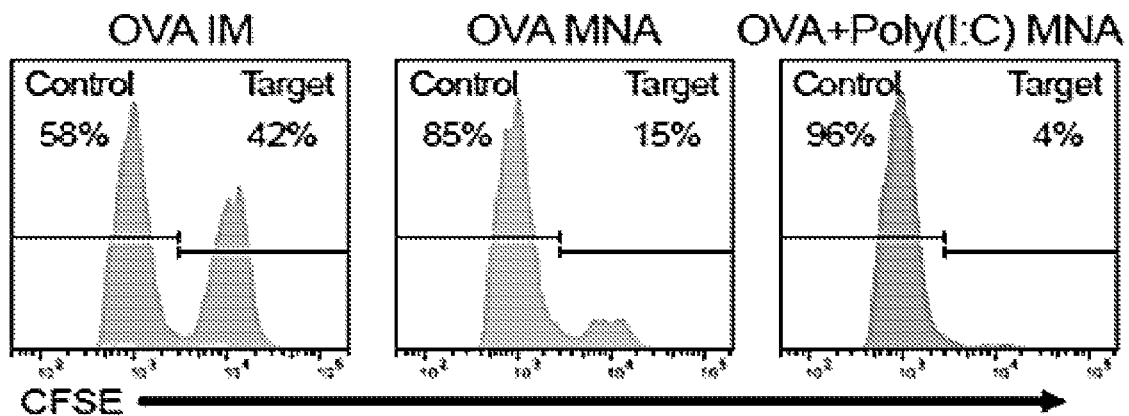
FIG. 11A illustrates representative histograms from flow cytometry analysis showing remaining CFSE-labeled cells in spleens of immunized and unimmunized mice.
Figure 11A:
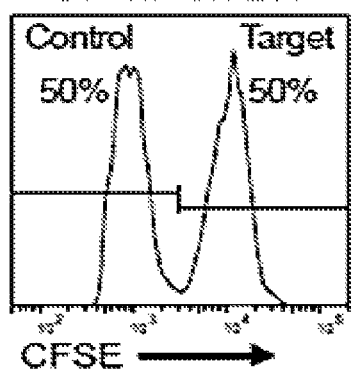
Figure 11B:
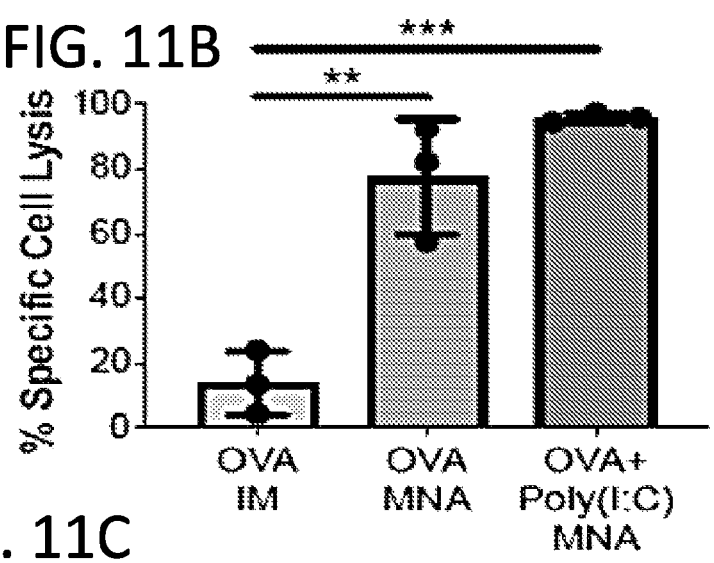
FIG. 11B shows quantification of specific cell lysis, with 100% lysis corresponding to complete elimination of target cells (mean±SD, 3 mice per group).

Upon demonstration of successful intradermal delivery of the vaccines in vivo, we specifically evaluated immunogenicity of MNA-embedded antigen±adjuvant and compared the MNA immunization to vaccination by the clinically common intramuscular (IM) injection route. To this end, CMC/Treh MNAs were fabricated with 10 µg OVA±25 µg Poly(I:C) per MNA as described above. We and others have previously shown that dissolving MNA integrated proteins maintained their integrity. For immunization, the vaccination regimen described in the methods section was followed for both IM and MNA immunizing mice through their abdomens. OVA-specific. cytotoxic-T-cell (CTL) and antibody responses were quantified using the standard in vivo lytic assay and ELISA, respectively. Cutaneous vaccination with MNAs elicited robust antigen-specific cellular immune responses (FIGS. 11A-B). As expected, equivalent numbers of antigen-pulsed (CFSEhigh) target cells and unpulsed (CFSElow) target cells were recovered from naïve or unimmunized mice (FIG. 11A), thereby indicating the absence of antigen-specific cytolytic activity. In contrast, specific lysis of antigen-pulsed target cells was dramatically enhanced in immunized mice, as shown by reduced survival of OVA-pulsed targets than unpulsed targets. Specifically, while minimal differences in recovery of two populations were observed in IM-OVA immunized mice (FIG. 11A), mice immunized with OVA-MNA demonstrated greater OVA-specific lysis in vivo, with significantly (as compared to IM-OVA) lower survival and recovery of OVA pulsed targets than unplused targets (FIG. 11A). Immunization with OVA+Poly(I:C) further improved the performance of vaccination (FIG. 11A). Quantification of antigen specific lysis by standard techniques confirmed that MNA immunization elicited potent CTL immunity (FIG. 11B), which was further improved by the inclusion of the adjuvant Poly(I:C). In comparison, IM immunization induced low level responses relative to unimmunized controls. Taken together, these results demonstrate that these MNAs can efficiently deliver antigens±adjuvants to APC rich microenvironments within the skin to induce potent CTL immune responses.

Figure 11C:
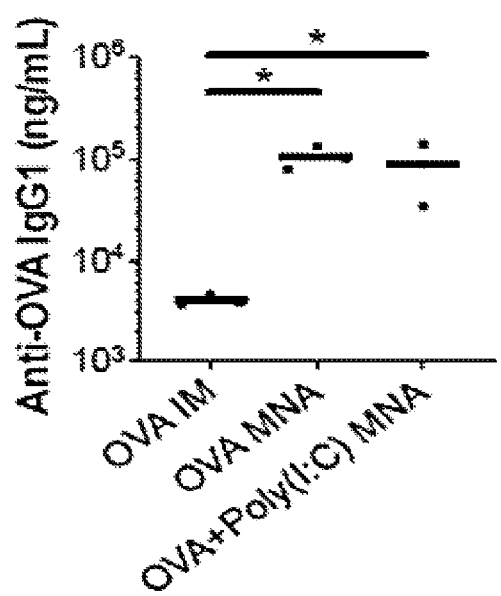
FIG. 11C shows serum concentrations of OVA-specific IgG1 and IgG2c antibodies (bars represent mean values, 3 mice per group).
Figure 11C:
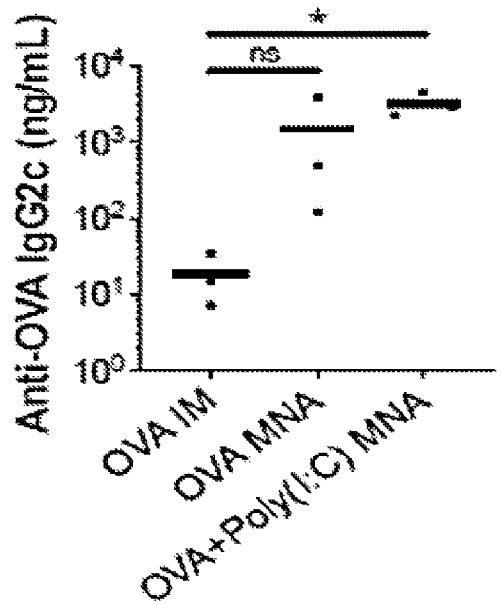

In addition to CTL immunity, cutaneous vaccination with MNAs elicited robust antigen-specific humoral immune responses (FIG. 11C). While vaccination of mice with both MNAs and IM resulted in IgG responses, those vaccinated with dissolving MNAs had significantly higher IgG titers, thereby indicating the importance of MNA technology in immunization efforts. Ultimately, the presented novel MNAs provide a unique opportunity for the specific and precise delivery of embedded antigen±adjuvant to defined microenvironments within the skin. For example, we and others have shown that the skin is rich in dendritic cells and other antigen presenting cells (APCs) essential for vaccine induced immune induction. Therefore, targeting skin APCs using MNAs can be an effective strategy for vaccination in general, and in particular for the induction of cell mediated immune responses, including CTL responses essential to prevent or treat many infectious diseases and cancer. As such, the presented MNA technology could enable capability relevant to a broad range of vaccination strategies.

Accordingly, the development and application of novel dissolving MNAs with undercut microneedles provide for effective intradermal vaccination. The unique MNA designs include pyramid heads and undercut stem regions with filleted bases. The manufacturing approach to create the undercut MNAs strategically involved 3D laser printing and a number of micromolding processes. Successful and reproducible fabrication of dissolvable MNAs with undercut needles that incorporate a myriad of biocargos was achieved using different biocompatible and water-soluble polymers. Importantly, the unprecedented level of geometric capability with 3D laser printing was demonstrated towards application-driven MNA designs for several cutaneous and non-cutaneous drug delivery applications. The introduced novel MNAs with undercut features fulfilled strength requirements for failure-free skin penetration in humans and mice, and successfully delivered their biocargos to targeted cutaneous microenvironments. Importantly, cutaneous vaccination using the model antigen-loaded MNAs (OVA-MNA) elicited significantly more potent antigen-specific cellular and humoral immune responses than those obtained by traditional intramuscular injection (IM-OVA) based immunization. Most importantly, MNA-directed co-delivery of the antigen (OVA) with the adjuvant (Poly(I:C)) improved the immunogenicity of the vaccine with respect to IM-based vaccination towards enhanced MNA-directed cutaneous vaccination. Taken together, the presented approach provides an effective means of fabricating novel dissolving MNAs for a broad range of cutaneous and non-cutaneous drug delivery applications.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method of forming a microneedle array comprising:
    forming a production mold of a flexible material, the production mold comprising a plurality of cavities, with each of the plurality of cavities being shaped to define a plurality of respective microneedles that each have a stem, a microneedle tip, a filleted base, and at least one undercut feature;

delivering a biodegradable matrix into each of the plurality of cavities of the production mold to form the stem, microneedle tip, and filleted base of each respective microneedle, wherein at least one bioactive material is incorporated into at least a portion of the biodegradable matrix, the biodegradable matrix comprising a first dissolvable material;

forming a backing layer adjacent a lower portion of the stem; and removing the microneedles from the production mold by pulling the microneedles out of the mold, wherein the at least a portion of the biodegradable matrix that includes the at least one bioactive material is delivered into at least the microneedle tip defined by the respective cavities of the production mold, wherein the flexible material has sufficient elasticity to allow for the molded microneedle array to be removed from the production mold in a single pull without damaging the integrity of the shape of the microneedles as defined by the mold, and wherein the backing layer is formed from a conformable material.

2. The method of claim 1, wherein the at least one undercut feature is directly below the microneedle tip.

3. The method of claim 1, wherein the stem is formed from the first dissolvable material.

4. The method of claim 1, wherein the stem is formed from a non-dissolvable material.

5. The method of claim 1, wherein the forming of the plurality of microneedles comprises providing a second dissolvable material into the production mold to form a dissolving layer at a portion of the stem that is adjacent the microneedle tip.

6. The method of claim 5, wherein the second dissolvable material of the dissolving layer is selected from a material that dissolves more quickly than the biodegradable matrix that contains the bioactive material.

7. The method of claim 1, wherein the backing layer is formed from the dissolvable material.

8. The method of claim 1, wherein the backing layer is formed from a non-dissolvable material.

9. The method of claim 1, wherein the first dissolvable material comprises carboxymethylcellulose, trehalose, polyvinylpyrrolidone, maltodextrin, silk, hyaluronic acid, poly(vinyl alcohol), polyethylene glycol, poly(lactic-co-glycolic acid), poly(lactic acid), or a combination thereof.

10. The method of claim 5, wherein the second dissolvable material comprises a small molecular weight, quickly dissolving polymer.

11. The method of claim 10, wherein the second dissolvable material is glucose, trehalose, sucrose, maltodextrin, polyvinylpyrrolidone, or a combination thereof.

12. The method of claim 1, wherein the conformable material is a non-dissolving polymer that can flex, deform, or bend to conform to non-uniform skin topography.

13. The method of claim 1, wherein the at least one bioactive material comprises two or more bioactive materials.

14. The method of claim 1, wherein the one or more bioactive materials comprises cosmetics, dermal-fillers, statins, growth factors, pain killers, anti-histamines, vitamins, anesthetics, anti-aging agents, small molecule drugs, haptens, allergens, anti-inflammatory agents, proteins, peptides, micro vesicles, exosomes, polyplexes (siRNA, shRNA, DNA vector complexes), recombinant viral vectors (i.e., Adenovirus, Lentivirus, Vaccinia Virus, Adeno-Associated Virus, and their different serotypes), monoclonal and polyclonal antibodies, and live or lysed cells.

15. The method of claim 1, wherein the plurality of microneedles has a shape that includes a circular obelisk, a square obelisk, a bevel obelisk, a pyramid on a square stem, an arrowhead shape on a stem, a pyramid head on a square obelisk stem, a conical head on a circular obelisk stem, a square obelisk, a 45° pyramid, or a 30° pyramid.

16. The method of claim 1, wherein the plurality of microneedles further comprises a fillet portion at the intersection of the backing layer and the stem.

17. A method of forming a flexible elastomer production mold comprising:

generating a 3D model drawing of a microneedle array that includes a plurality of microneedles with at least one undercut feature, at least one fillet feature, and at least one backing layer;

forming a master microneedle array from the 3D model drawing using 3D laser printing with a wear-resistant resin;

forming a negative elastomer mold from the master microneedle array, wherein the negative elastomer mold comprises microneedle-shaped wells with the at least one undercut feature and the at least one fillet feature;

forming at least one replica of the master microneedle array from the negative elastomer mold via UV-curable micromolding; and forming the production mold of the microneedle array using the at least one replica, wherein the production mold is formed of a flexible material.

18. The method of claim 17, wherein the flexible material has sufficient elasticity to allow for a molded microneedle array to be removed from the production mold in a single pull without damaging the integrity of the shape of the plurality microneedles as defined by the production mold.

19. The method of claim 17, wherein the at least one replica includes a plurality of replicas, and the forming of the production mold comprises forming a microneedle array holder and combining the plurality of replicas together on the microneedle array holder.

20. The method of claim 19, wherein the microneedle array holder is formed of a resin material.

* * * * *